United States Patent
Okubayashi et al.

(10) Patent No.: US 8,436,078 B2
(45) Date of Patent: *May 7, 2013

(54) DENTAL COMPOSITION AND COMPOSITE RESIN

(75) Inventors: Masaki Okubayashi, Kurashiki (JP); Koichi Okada, Tokyo (JP); Yusuke Takahata, Kurashiki (JP); Keisuke Ohtsuka, Kitakyushu (JP)

(73) Assignees: Kuraray Noritake Dental Inc., Kurashiki-shi (JP); JGC Catalysts and Chemicals Ltd., Kawasaki-shi (JP)

(*) Notice: Subject to any disclaimer, the term of this patent is extended or adjusted under 35 U.S.C. 154(b) by 183 days.

This patent is subject to a terminal disclaimer.

(21) Appl. No.: 12/989,962

(22) PCT Filed: Apr. 28, 2009

(86) PCT No.: PCT/JP2009/058417
§ 371 (c)(1),
(2), (4) Date: Oct. 28, 2010

(87) PCT Pub. No.: WO2009/133913
PCT Pub. Date: Nov. 5, 2009

(65) Prior Publication Data
US 2011/0046260 A1   Feb. 24, 2011

(30) Foreign Application Priority Data

Apr. 28, 2008 (JP) .................... 2008-117803

(51) Int. Cl.
*A61K 6/08* (2006.01)
*A61C 5/09* (2006.01)
*B32B 18/00* (2006.01)

(52) U.S. Cl.
USPC ........ 523/216; 523/116; 428/404; 433/222.1; 433/228.1

(58) Field of Classification Search ............ 523/116, 523/216; 428/404; 433/228.1
See application file for complete search history.

(56) References Cited

U.S. PATENT DOCUMENTS

| | | | |
|---|---|---|---|
| 2,913,419 A * | 11/1959 | Alexander | 516/80 |
| 4,719,297 A | 1/1988 | Henne et al. | |
| 5,055,497 A | 10/1991 | Okada et al. | |
| 5,192,815 A | 3/1993 | Okada et al. | |
| 5,795,497 A | 8/1998 | Kimura et al. | |
| 5,846,310 A * | 12/1998 | Noguchi et al. | 106/482 |
| 6,849,112 B2 | 2/2005 | Nishida et al. | |
| 6,849,670 B2 | 2/2005 | Satoh et al. | |
| 6,933,327 B2 | 8/2005 | Yamakawa et al. | |
| 7,981,513 B2 * | 7/2011 | Ohtsuka et al. | 428/403 |
| 2002/0022677 A1 | 2/2002 | Teramae et al. | |
| 2004/0151691 A1 | 8/2004 | Oxman et al. | |
| 2005/0113480 A1 | 5/2005 | Usuki et al. | |
| 2009/0253825 A1 | 10/2009 | Ohtsuka et al. | |
| 2010/0056664 A1 | 3/2010 | Ohtsuka et al. | |

FOREIGN PATENT DOCUMENTS

| | | |
|---|---|---|
| EP | 0009348 | 4/1980 |
| JP | 57 197289 | 12/1982 |
| JP | 63 088110 | 4/1988 |
| JP | 2 028204 | 1/1990 |
| JP | 2 134307 | 5/1990 |
| JP | 6 107516 | 4/1994 |
| JP | 9 169613 | 6/1997 |
| JP | 9 255516 | 9/1997 |
| JP | 10 001473 | 1/1998 |
| JP | 11 092461 | 4/1999 |
| JP | 2000 159621 | 6/2000 |
| JP | 2001 139411 | 5/2001 |
| JP | 2001 302429 | 10/2001 |
| JP | 2002 138008 | 5/2002 |
| JP | 2002 204803 | 7/2002 |
| JP | 2003 146822 | 5/2003 |
| JP | 34 21072 | 6/2003 |
| JP | 2005 154312 | 6/2005 |
| JP | 2006 052128 | 2/2006 |
| JP | 2006-052128 A * | 2/2006 |
| JP | 2006 516544 | 7/2006 |
| JP | 2007 261967 | 10/2007 |
| JP | 2008 115136 | 5/2008 |
| WO | 02 05752 | 1/2002 |
| WO | 2007 111066 | 10/2007 |
| WO | WO2008/056485 * | 5/2008 |

OTHER PUBLICATIONS

International Search Report issued Jun. 9, 2009 in PCT/JP09/058417 filed Apr. 28, 2009.
International Search Report issued Jul. 28, 2009 in PCT/JP09/058415 filed Apr. 28, 2009.
International Search Report issued Jul. 28, 2009 in PCT/JP09/058416 filed Apr. 28, 2009.
U.S. Appl. No. 12/990,077, filed Oct. 28, 2010, Kuboe, et al.
U.S. Appl. No. 12/989,996, filed Oct. 28, 2010, Okubayashi, et al.

* cited by examiner

*Primary Examiner* — Tae H Yoon
(74) *Attorney, Agent, or Firm* — Oblon, Spivak, McClelland, Maier & Neustadt, L.L.P.

(57) ABSTRACT

The present invention provides a dental composition exhibiting both an excellent light diffusion property and excellent transparency, and having high mechanical strength and surface smoothness and gloss after polishing as a cured product and good handling properties as a paste. The present invention is a dental composition including: a polymerizable monomer (A); and an amorphous powder (B). The amorphous powder (B) has an average particle size of 1 to 20 μm, and includes silica-based fine particles and coatings of an oxide that cover the surfaces of the silica-based fine particles. The oxide contains a zirconium atom, a silicon atom, and an oxygen atom. The difference in refractive index between the cured product of the polymerizable monomer (A) and the amorphous powder (B) is 0.005 to 0.03.

20 Claims, 1 Drawing Sheet

DENTAL COMPOSITION AND COMPOSITE RESIN

TECHNICAL FIELD

The present invention relates to a dental composition that can be used suitably as a dental material, particularly a dental composite resin, that can be used as a substitute for a part of a natural tooth or an entire natural tooth in the field of dental treatment.

BACKGROUND ART

A dental composite material containing a polymerizable monomer, a filler, and a polymerization initiator is called a composite resin, and this dental material is most widely used today as a restorative material for repairing fractures of teeth and dental caries. Such a dental composite material is required to have the following properties. Specifically, as a cured product obtained after polymerization curing, the dental composite material is required to have sufficient mechanical strength and hardness to serve as a substitute for natural teeth, wear resistance against occlusion of teeth in an oral cavity, surface smoothness and gloss, color matching with natural teeth, transparency, etc. Furthermore, as a paste which has not yet been polymerized and cured, the dental composite material is desired to have ease of handling (high handling properties) for dental clinicians and technicians, for example, proper fluidity and forming property, no adhesion to dental instruments, no stickiness, etc.

These properties of the dental composite material are greatly influenced by the component materials, shape, particle size, and content of fillers used therein and by the combination of the fillers used together. For example, when an inorganic filler having an average particle size of more than 1 μm is used, the filling rate of the filler in the polymerizable monomer can be increased easily and therefore sufficient mechanical strength as a cured product and high handling properties as a paste can be obtained. The use of such an inorganic filler has, however, a drawback in that it is difficult to obtain satisfactory gloss even after final polishing, and even if satisfactory gloss is obtained, the gloss cannot be retained for a long time. On the other hand, when an inorganic ultrafine particle filler having an average particle size of 1 μm or less is used, the surface smoothness and gloss after polishing of the cured product and the gloss durability in the oral cavity are improved. The use of such an inorganic ultrafine particle filler has, however, a drawback in that when the inorganic filler is mixed and kneaded with the polymerizable monomer, the viscosity of the resulting paste increases significantly, which makes it difficult to increase the content of the filler. As a result, the mechanical strength of the cured product decreases, and the unpolymerized pasty composition becomes sticky, which reduces the handling properties. Furthermore, when an organic-inorganic composite filler obtained by mixing inorganic ultrafine particles having an average particle size of 100 nm or less with a polymerizable monomer, curing the mixture, and grinding the resulting cured product is used, the handling properties of the paste are improved, but the content of the inorganic filler in the cured product still is insufficient. Since the surface of the organic-inorganic composite filler forms a weak bond with the matrix, the mechanical strength of the cured product is not sufficient. Under these circumstances, it is difficult to increase the mechanical strength and the surface smoothness and gloss after polishing of the cured product and the handling properties of the paste in a balanced manner.

On the other hand, in recent years, dental composite materials have been required not only to have the above-mentioned properties but also to match natural teeth, that is, to have colors and optical properties such as transparency and a light diffusion property similar to natural teeth. Studies have been conducted to impart these properties to dental composite materials. JP 09(1997)-169613 A describes a dental composite restorative material containing a polymerizable monomer, a first filler, and a second filler. The first filler has a refractive index difference of 0.06 or less from the cured polymerizable monomer. The second filler has a refractive index difference of more than 0.06 from the cured polymerizable monomer, and has an average particle size of 1 μm or more. In this dental composite restorative material, the degree of diffusion D represented by the following formula (1) has a value of 0.002 to 0.3:

$$D=(I_{20}/\cos 20°+I_{70}/\cos 70°)/(2I_0) \quad (1)$$

where I denotes the intensity of transmitted light through a sample, and $I_0$, $I_{20}$ and $I_{70}$ denote the intensities (the intensities of light) of the transmitted light measured at angles of 0, 20, and 70 degrees respectively with respect to the direction perpendicular to the sample plate (the incident direction of the light).

JP 09(1997)-255516 A describes a dental composite material containing a polymerizable monomer, one kind of filler, and another kind of filler. The former filler is obtained by aggregating inorganic filler particles having an average particle size of 0.01 to 1 μm and subjecting the resulting aggregate to heat treatment, and has a refractive index difference of 0.06 or less from the cured polymerizable monomer. The latter filler has a refractive index difference of more than 0.06 from the cured polymerizable monomer, and has an average particle size of 1 μm or more. The degree of diffusion D represented by the above formula (1) has a value of 0.002 to 0.3.

JP 2002-138008 A describes a dental curable composition containing a polymerizable monomer, and an organic-inorganic composite filler having a refractive index difference of 0.01 or more as an absolute value from the cured polymerizable monomer, and having an average particle size of 1 to 20 μm. In this dental curable composition, the degree of diffusion D represented by the above formula (1) has a value of 0.01 or more.

The dental composite restorative material described in JP 09(1997)-169613 A or JP 09(1997)-255516 A matches natural teeth very well because the combination of the polymerizable monomer and two kinds of fillers having different refractive indices imparts a light diffusion property to the cured product. In addition, the cured product of this dental composite material has sufficient polishability because the inorganic filler has a primary particle size of 1 μm or less. However, the use of two kinds of inorganic fillers having different refractive indices makes it difficult to obtain sufficient transparency as a dental material, and there is room for improvement.

The dental curable composition described in JP 2002-138008 A uses an organic-inorganic composite filler having a refractive index difference of 0.01 or more from the cured polymerizable monomer and having an average particle size of 1 to 20 μm, and the use of this filler imparts surface smoothness and gloss after polishing and a light diffusion property to the cured product. The use of the organic-inorganic composite filler, however, makes the bond with the polymerizable monomer as a matrix insufficient. As a result, sufficient mechanical strength cannot be obtained, and there is room for improvement.

CITATION LIST

Patent Literature 1 JP 09(1997)-169613 A
Patent Literature 2 JP 09(1997)-255516 A
Patent Literature 3 JP 2002-138008 A

SUMMARY OF INVENTION

The present invention has been made in order to solve the above conventional problems, and it is an object of the present invention to provide a dental composition exhibiting both an excellent light diffusion property and excellent transparency, and having excellent mechanical strength and surface smoothness and gloss after polishing as a cured product and good handling properties as a paste. It is another object of the present invention to provide a composite resin exhibiting both an excellent light diffusion property and excellent transparency, and having excellent mechanical strength and surface smoothness and gloss after polishing as a cured product and good handling properties as a paste.

The present invention that has solved the above problems is a dental composition including: a polymerizable monomer (A); and an amorphous powder (B). The amorphous powder (B) has an average particle size of 1 to 20 µm and includes silica-based fine particles and coatings of an oxide that cover the surfaces of the silica-based fine particles. The oxide contains a zirconium atom, a silicon atom, and an oxygen atom. In this dental composition, a difference in refractive index between a cured product of the polymerizable monomer (A) and the amorphous powder (B) is 0.005 to 0.03.

The present invention also is a composite resin using the above dental composition.

According to the dental composition of the present invention, a cured product having both a good light diffusion property and a high transparency can be obtained. In addition, the cured product also has high surface smoothness and gloss after polishing and high gloss durability, and therefore, the dental composition of the present invention has a good aesthetic appearance. According to the dental composition of the present invention, a cured product having high mechanical strength can be obtained. Furthermore, the dental composition of the present invention has, as a paste, good handling properties and proper fluidity and forming property, and the adhesion to dental instruments and stickiness are reduced. That is, this dental composition is very easy to handle. The dental composition of the present invention can be used particularly suitably as a composite resin, and this composite resin exhibits both an excellent light diffusion property and excellent transparency, and has excellent mechanical strength and surface smoothness and gloss after polishing as a cured product and good handling properties as a paste.

DESCRIPTION OF EMBODIMENTS

Figure 1:
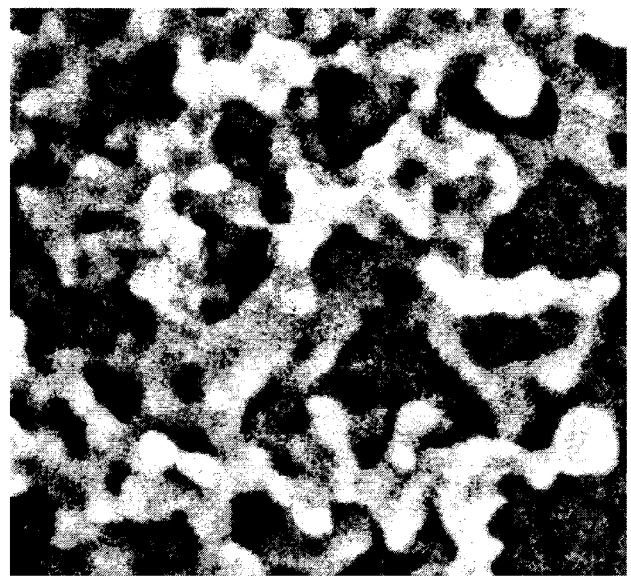
FIG. 1 is an SEM micrograph (×500000) of one example of an amorphous powder (B) which has been subjected to a drying process.

For the polymerizable monomer (A) in the present invention, a known polymerizable monomer can be used without any limitation as long as the difference between the refractive index of the cured product of the polymerizable monomer (A) and that of the amorphous powder (B) is 0.005 to 0.03. For ease of approximation to the refractive indices of the amorphous powder (B) and inorganic particles (C) to be described later, the refractive index of the cured product is preferably 1.45 to 1.65, more preferably 1.50 to 1.60, and particularly preferably 1.52 to 1.58. To obtain a desired refractive index after the curing of the polymerizable monomer (A), several kinds of polymerizable monomers having different refractive indices may be mixed at an appropriate ratio, with taking into consideration that a polymer obtained by polymerizing a polymerizable monomer generally tends to have a slightly higher refractive index than the polymerizable monomer itself.

Among the above-mentioned polymerizable monomers (A), a radical polymerizable monomer is used suitably. Specific examples of the radical polymerizable monomer in the polymerizable monomer (A) include esters of α-cyanoacrylic acid, (meth)acrylic acid, α-halogenated acrylic acid, crotonic acid, cinnamic acid, sorbic acid, maleic acid, itaconic acid, etc., (meth)acrylamide, (meth)acrylamide derivatives, vinyl esters, vinyl ethers, mono-N-vinyl derivatives, styrene derivatives, and the like. Among them, (meth)acrylic acid esters are preferred. In the present invention, "(meth)acryl" means methacryl or acryl.

Examples of (meth)acrylic acid ester-based polymerizable monomers are given hereinbelow.

(1) Monofunctional (meth)acrylates include:
methyl(meth)acrylate, isobutyl(meth)acrylate, benzyl (meth)acrylate, lauryl(meth)acrylate, 2-(N,N-dimethylamino)ethyl(meth)acrylate, 2,3-dibromopropyl(meth)acrylate, 2-hydroxyethyl(meth)acrylate, 6-hydroxyhexyl (meth)acrylate, 10-hydroxydecyl(meth)acrylate, propylene glycol mono(meth)acrylate, glycerol mono(meth)acrylate, erythritol mono(meth)acrylate, N-methylol (meth)acrylamide, N-hydroxyethyl(meth)acrylamide, N-(dihydroxyethyl) (meth)acrylamide, (meth)acryloyloxydodecylpyridinium bromide, (meth)acryloyloxydodecylpyridinium chloride, (meth)acryloyloxyhexadecylpyridinium chloride, (meth)acryloyloxydecylammonium chloride, and the like.

(2) Bifunctional (meth)acrylates include:
ethylene glycol di(meth)acrylate, triethylene glycol di(meth)acrylate, propylene glycol di(meth)acrylate, neopentyl glycol di(meth)acrylate, 1,6-hexanediol di(meth)acrylate, 1,10-decanediol di(meth)acrylate, bisphenol A diglycidyl (meth)acrylate (2,2-bis[4-[3-(meth)acryloyloxy-2-hydroxypropoxy]phenyl]propane, commonly known as "BisGMA"), 2,2-bis[4-(meth)acryloyloxyethoxyphenyl]propane, 2,2-bis[4-(meth)acryloyloxypolyethoxyphenyl]propane, 2,2-bis[4-[3-((meth)acryloyloxy-2-hydroxypropoxy]phenyl]propane, 1,2-bis[3-(meth)acryloyloxy-2-hydroxypropoxy]ethane, pentaerythritol di(meth)acrylate, [2,2,4-trimethylhexamethylenebis(2-carbamoyloxyethyl)] dimethacrylate (commonly known as "UDMA"), and the like.

(3) Trifunctional or higher polyfunctional (meth)acrylates include:
trimethylolpropane tri(meth)acrylate, trimethylolethane tri(meth)acrylate, tetramethylolmethane tri(meth)acrylate, pentaerythritol tetra(meth)acrylate, dipentaerythritol hexa (meth)acrylate, N,N'-(2,2,4-trimethylhexamethylene)bis[2-(aminocarbonyloxy)propane-1,3-diol]tetramethacrylate, 1,7-diacryloyloxy-2,2,6,6-tetraacryloyloxymethyl-4-oxyheptane, and the like.

Any one of the above-mentioned polymerizable monomers can be used alone or as a mixture of two or more kinds thereof.

To improve the adhesion to tooth structures, metals, ceramics, and the like, it is preferable in some cases that the polymerizable composition of the present invention contain, as a polymerizable monomer, a functional monomer for providing adhesion to these adherends.

As such functional monomers, for example, monomers having a phosphoric acid group, such as 2-(meth)acryloyloxyethyl dihydrogenphosphate, 10-(meth)acryloyloxydecyl dihydrogenphosphate, and 2-(meth)acryloyloxyethyl phenyl hydrogenphosphate, and monomers having a carboxylic acid group, such as 11-(meth)acryloyloxy-1,1-undecanedicarboxylic acid and 4-(meth)acryloyloxyethoxycarbonyl phthalic acid are preferred because these monomers exhibit excellent adhesion to tooth structures and base metals.

As such functional monomers, for example, 10-mercaptodecyl(meth)acrylate, 6-(4-vinylbenzyl-n-propyl)amino-1,3,5-triazine-2,4-dithione, a thiouracil derivative described in JP 10(1998)-1473 A, and a sulfur element-containing compound described in JP 11(1999)-92461 A are preferred because these monomers exhibit excellent adhesion to precious metals.

Furthermore, as such a functional monomer, for example, a silane coupling agent such as γ-methacryloxypropyl trimethoxysilane is effective in bonding to ceramics, porcelains, and dental composite resins.

In the present invention, an amorphous powder (B) including silica-based fine particles and coatings of an oxide that cover the surfaces of the silica-based fine particles is used. The oxide contains a zirconium atom, a silicon atom, and an oxygen atom.

In the present invention, an "amorphous" powder means that when this inorganic powder is subjected to an X-ray diffraction analysis by X-ray diffractometry using an X-ray diffractometer ("RINT-1400" manufactured by Rigaku Corporation) under the following conditions, no diffraction peak is observed.

(Conditions for X-Ray Diffraction Analysis)
2θ: 10-70 degrees
Scan speed: 2 degrees/min
Tube voltage: 30 kV
Tube current: 130 mA The silica-based fine particles mean fine particles containing 80 mol % or more of $SiO_2$ in terms of oxides. The components other than $SiO_2$ are not particularly limited as long as they do not impair the advantageous effects of the present invention. Examples of the components include $TiO_2$, $ZrO_2$, $Al_2O_3$, and $Na_2O$. Preferably, the content of $SiO_2$ is 90 mol % or more. It is preferable that the content of $SiO_2$ be substantially 100 mol % (that is, the content be 100% except for unavoidable impurities). Preferably, the average particle size of the silica-based fine particles is 2 to 300 nm. When the average particle size is less than 2 nm, the resulting cured product of the dental composition may have insufficient mechanical strength. When the dental composition containing the silica-based fine particles having an average particle size of more than 300 nm is used to restore teeth, the cured product may have insufficient surface smoothness and gloss after polishing. The average particle size of the silica-based fine particles can be determined by the dynamic light scattering method. For example, 7.0 g of an aqueous dispersion sol containing silica-based fine particles (having a solid content of 20% by weight) is placed in a cylindrical stainless steel cell with a size of 3 cm length, 2 cm width and 2 cm height equipped with a transmission window, and the particle size distribution is measured using an ultrafine particle size distribution analyzer of dynamic light scattering type (Model 9340-UPA150 manufactured by Honeywell). Thus, the average particle size can be calculated.

The oxide that covers the surface of the silica-based fine particle contains a zirconium atom, a silicon atom, and an oxygen atom. The oxide further may contain a titanium atom, an aluminum atom, etc. This oxide coating on the surface of the silica-based fine particle approximates the refractive index of the amorphous powder (B) to that of the polymerizable monomer (A). As a result, the dental composition exhibits excellent transparency and an excellent light diffusion property, and the cured product of the dental composition has high mechanical strength.

Specific examples of the structure of the oxide are shown below.

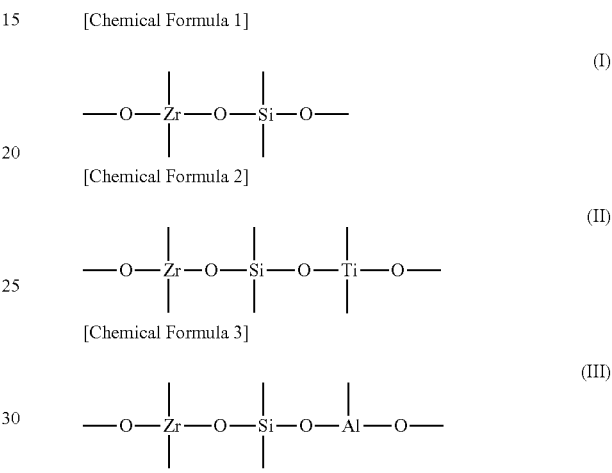

In the amorphous powder (B), the oxide coating may cover each of the silica-based fine particles, or may cover a plurality of silica-based fine particles. In the preferred embodiment, the oxide coating covers a plurality of silica-based fine particles. In this case, the amorphous powder (B) has a structure in which the oxide coating of a silica-based fine particle and the oxide coating of a neighboring silica-based fine particle are connected with each other. In this regard, it is preferable that the amorphous powder (B) have a structure in which the oxide coating of a silica-based fine particle and the oxide coating of a neighboring silica-based fine particle extend and are connected with each other. In the case where the silica-based fine particles are connected through the oxide coatings in the manner as described above, the silica-based fine particles are bonded to each other more strongly than they are aggregated together by intermolecular force. Accordingly, the use of this amorphous powder (B) in the dental material further increases the mechanical strength. Furthermore, as the dental material is abraded, the connecting portion between the oxide coatings is ruptured and thereby only a part of the amorphous powder (B) comes off. Therefore, the use of this amorphous powder (B) also increases the surface smoothness and gloss after polishing. From the viewpoint of the surface smoothness and gloss after polishing, it is preferable that, in the outer shape of this connection structure, the connecting portion between the oxide coatings be thinner than a portion where the silica-based fine particle is covered by the oxide coating. In other words, it is preferable that the thickness of the connecting portion between the oxide coatings be smaller than the sum of the largest dimension of the silica-based fine particle in the thickness direction and the thicknesses of two portions of the oxide coating of that particle.

Figure 2:
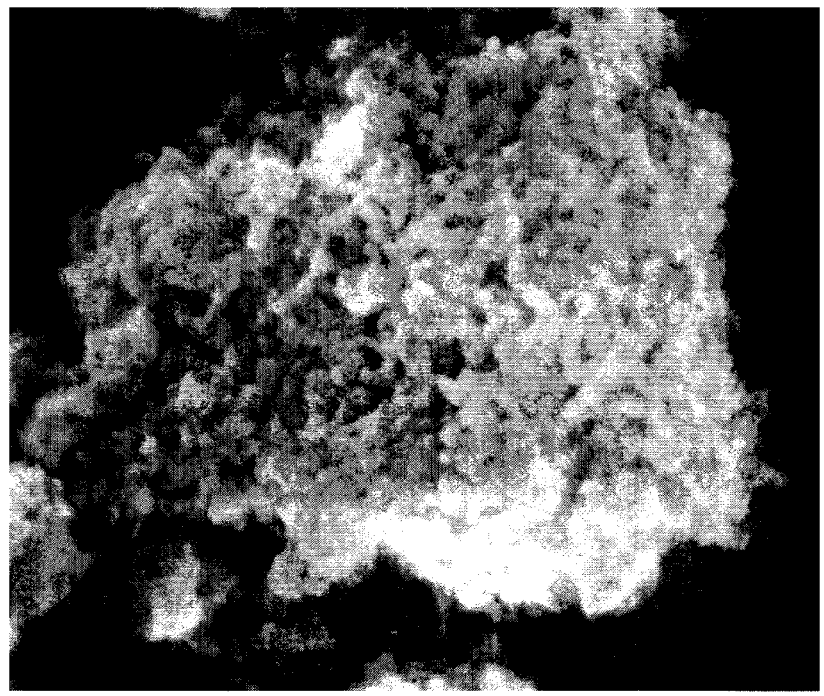
FIG. 2 is an SEM micrograph (×300000) of another example of an amorphous powder (B) which has been subjected to a drying process.

It is more preferable, in the structure of the amorphous powder (B), that one oxide coating of a silica-based fine particle is connected with a plurality of oxide coatings of neighboring silica-based fine particles. In this case, the amorphous powder (B) may have a structure, such as a tetrapod structure, or a star structure, in which a plurality of silica-based fine particles are connected through the oxide coatings to one silica-based fine particle with the one silica-based fine particle being placed in the center of the structure, or may have a branched three-dimensional network structure, in which the plurality of silica-based fine particles connected to one silica-based fine particle through the oxide coatings are connected further with other silica-based fine particles. In this three-dimensional network structure, silica-based fine particles are present at the ends of the branches and the branch points. Silica-based fine particles may be present at positions other than the ends of the branches and the branch points. It is particularly preferable that the amorphous powder (B) have a porous particle structure in which the oxide coatings are connected to each other to form an aggregate of the silica-based fine particles covered with the oxide coatings. FIG. 1 and FIG. 2 show SEM micrographs of examples of the amorphous powder (B) used in the present invention.

The thickness of the oxide coating may be determined appropriately in consideration of the particle size of the above silica-based fine particles, the thickness of the surface-treated layer to be described later, and the particle size of the amorphous powder (B) to be described later.

The surface of the amorphous powder (B) may be treated, if necessary, with at least one organic metal compound selected from the group consisting of an organic silicon compound, an organic titanium compound, an organic zirconium compound, and an organic aluminum compound. That is, a surface-treated layer may be formed on the oxide coating of the amorphous powder (B). This surface treatment improves the affinity between the polymerizable monomer (A) and the amorphous powder (B), and thereby enhances the dispersibility and adhesion. As a result, the mechanical strength of the cured product can be increased. When two or more different kinds of organic metal compounds are used, the surface-treated layer may be made of a mixture of these two or more different kinds of organic metal compounds, or may have a multilayer structure in which the two or more different organic metal compound layers are laminated.

An example of the organic silicon compound is a compound represented by $R^1{}_n SiX_{4-n}$ (where $R^1$ is a substituted or unsubstituted hydrocarbon group having 1 to 12 carbon atoms, X is an alkoxy group having 1 to 4 carbon atoms, a hydroxyl group, a halogen atom, or a hydrogen atom, and n is an integer of 0 to 3. If a plurality of $R^1$s and a plurality of Xs are present, the $R^1$s may be the same as or different from one another, and the Xs may be the same as or different from one another.)

Specific examples of the organic silicon compound include methyltrimethoxysilane, dimethyldimethoxysilane, phenyltrimethoxysilane, diphenyldimetoxysilane, methyltriethoxysilane, dimethyldiethoxysilane, phenyltriethoxysilane, diphenyldiethoxysilane, isobutyltrimethoxysilane, vinyltrimethoxysilane, vinyltriethoxysilane, vinyl-tris(β-methoxyethoxy)silane, 3,3,3-trifluoropropyl trimethoxysilane, methyl-3,3,3-trifluoropropyl dimethoxysilane, β-(3,4-epoxycyclohexyl)ethyltrimethoxysilane, γ-glycidoxypropyltrimethoxysilane, γ-glycidoxypropylmethyldiethoxysilane, γ-glycidoxypropyltriethoxysilane, γ-methacryloxypropylmethyldimethoxysilane, γ-methacryloxypropylmethyldiethoxysilane, N-β(aminoethyl)γ-aminopropylmethyldimethoxysilane, N-β(aminoethyl)γ-aminopropyltrimethoxysilane, N-β(aminoethyl)γ-aminopropyltriethoxysilane, γ-aminopropyltrimethoxysilane, γ-aminopropyltriethoxysilane, N-phenyl-γ-aminopropyltrimethoxysilane, γ-mercaptopropyltrimethoxysilane, trimethylsilanol, methyltrichlorosilane, methyldichlorosilane, dimethyldichlorosilane, trimethylchlorosilane, phenyltrichlorosilane, diphenyldichlorosilane, vinyltrichlorosilane, trimethylbromosilane, diethylsilane, vinyltriacetoxysilane, ω-(meth)acryloxyalkyl trimethoxysilane (having 3 to 12 carbon atoms between a (meth)acryloxy group and a silicon atom, for example, γ-methacryloxypropyltrimethoxysilane, or the like), ω-(meth)acryloxyalkyl triethoxysilane (having 3 to 12 carbon atoms between a (meth)acryloxy group and a silicon atom, for example, γ-methacryloxypropyltriethoxysilane, or the like), and the like.

Among them, a coupling agent having a functional group that is copolymerizable with the polymerizable monomer (A), for example, ω-(meth)acryloxyalkyl trimethoxysilane (having 3 to 12 carbon atoms between a (meth)acryloxy group and a silicon atom), ω-(meth)acryloxyalkyl triethoxysilane (having 3 to 12 carbon atoms between a (meth)acryloxy group and a silicon atom), vinyltrimethoxysilane, vinyltriethoxysilane, vinyltriacetoxysilane, γ-glycidoxypropyltrimethoxysilane, or the like is used particularly preferably.

Examples of the organic titanium compound include tetramethyl titanate, tetraisopropyl titanate, tetra-n-butyl titanate, butyl titanate dimmer, and tetra(2-ethylhexyl)titanate.

Examples of the organic zirconium compound include zirconium isopropoxide, zirconium-n-butoxide, zirconium acetylacetonate, and zirconyl acetate.

Examples of the organic aluminum compound include aluminum acetylacetonate and a chelate compound of a salt of aluminum and an organic acid.

Furthermore, since the amorphous powder (B) contained in the dental composition of the present invention contains metal elements such as aluminum, zirconium, and titanium, an organic phosphorus compound disclosed in JP 02(1990)-28204 A also is used preferably as a surface treating agent in some cases.

The average particle size of the amorphous powder (B) is 1 (more accurately 1.0) to 20 μm, preferably 2 to 15 μm, and more preferably 3 to 10 μm. When the average particle size is less than 1 μm, the resulting paste becomes sticky, which causes insufficient handling properties. When the average particle size exceeds 20 μm, the sagging of the paste develops, which impairs the handling properties. If the amorphous powder (B) consists of aggregated particles, the above-mentioned average particle size is the average particle size of the aggregated particles.

The average particle size of the amorphous powder (B) can be obtained by the laser diffraction/scattering method. More specifically, for example, the average particle size can be obtained by the measurement using a 0.2% aqueous solution of sodium hexametaphosphate as a dispersion medium, with a laser diffraction particle size distribution analyzer (SALD-2100 manufactured by Shimadzu Corporation).

The overall shape of the particles of the amorphous powder (B) is not particularly limited. The amorphous powder (B) can be used as an irregular-shaped or nearly spherical (or spherical) powder. If the irregular-shaped amorphous powder (B) is used, the mechanical strength and wear resistance are particularly excellent, and if the nearly spherical (or spherical) amorphous powder (B) is used, the surface smoothness and gloss after polishing and the gloss durability are particularly excellent. The shape of the amorphous powder (B) may be selected suitably in accordance with the intended use of the dental composition.

The refractive index of the amorphous powder (B) is not particularly limited as long as the difference in refractive index from the cured product of the above-described polymerizable monomer (A) is 0.005 to 0.03. For ease of approximation to the refractive indices of the cured product of the above-described polymerizable monomer (A) and the inorganic particles (C) to be described later, the refractive index of the amorphous powder (B) is preferably 1.45 to 1.65, more preferably 1.50 to 1.60, and particularly preferably 1.52 to 1.58. The refractive index of the amorphous powder (B) can be controlled by adjusting the content ratio of the metal elements in the above-mentioned oxide, adjusting the thickness of the oxide coating, etc.

The amount of the amorphous powder (B) to be added is preferably 50 to 400 parts by weight per 100 parts by weight of the polymerizable monomer (A), more preferably 75 to 350 parts by weight, and particularly preferably 100 to 300 parts by weight. In the dental composition of the present invention, the amorphous powder (B) has a structure in which surfaces of silica-based fine particles are covered with coatings of an oxide containing a zirconium atom, a silicon atom, an oxygen atom, etc. Therefore, a sufficient light diffusion property is obtained even when there is only a small difference in refractive index of 0.005 to 0.03 from the polymerizable monomer (A). This unique structure of the amorphous powder (B) allows the content of the amorphous powder (B) to be high while the increase in the viscosity and the stickiness of the paste are prevented. As a result, the mechanical strength also can be increased further.

There is no particular limitation on the production method of the amorphous powder (B). For example, the amorphous powder (B) can be produced by the following steps:

(1) adding a hydroxide of an alkali metal and hydrogen peroxide to an aqueous solution containing a zirconium oxide hydrate and stirring the mixture to prepare a mixed aqueous solution in which the zirconium oxide hydrate is peptized;

(2) adding, under stirring, the mixed aqueous solution obtained in the above step (1) and an aqueous solution of a silicic acid solution to a silica sol in which silica-based fine particles having an average particle size of 2 to 300 nm are dispersed in water;

(3) treating the mixed aqueous solution obtained in the above step (2) with a cation-exchange resin to remove alkali cations;

(4) putting the mixed aqueous solution obtained in the above step (3) into a reaction vessel and subjecting the mixed aqueous solution to a hydrothermal treatment at a temperature of 100 to 350° C. to prepare a mixed aqueous solution containing the amorphous powder (B) in which the surfaces of the silica-based fine particles are covered with coatings of an oxide containing at least a zirconium atom, a silicon atom, and an oxygen atom; and (5) drying the amorphous powder (B) contained in the mixed aqueous solution obtained in the above step (4).

The zirconium oxide hydrate ($ZrO_2 \cdot xH_2O$) used in the step (1) can be prepared by a conventionally known method, for example, by hydrolyzing a zirconium salt in an aqueous solution, or by adding alkali or ammonia to an aqueous solution of a zirconium salt to cause a neutralization reaction. The zirconium oxide hydrate is obtained, for example, by adding, under stirring, ammonia or aqueous ammonia to an aqueous solution of one or more zirconates selected from zirconium oxychloride, zirconium oxysulfate, zirconium oxynitrate, zirconium oxyacetate, zirconium oxycarbonate, and ammonium zirconium oxycarbonate to obtain a neutralized reaction product, and washing the neutralized reaction product.

The hydroxide of an alkali metal ($M_2O$) used in the above step (1) is, for example, potassium hydroxide, sodium hydroxide, etc. Among them, potassium hydroxide is used preferably.

Preferably, this hydroxide of an alkali metal is added at a molar ratio to the zirconium oxide hydrate ($M_2O/ZrO_2 \cdot xH_2O$) of 1/1 to 10/1.

Preferably, the hydrogen peroxide ($H_2O_2$) used in the above step (1) is added at a molar ratio to the zirconium oxide hydrate ($H_2O_2/ZrO_2 \cdot xH_2O$) of 5/1 to 30/1.

As the silica sol used in the above step (2), any commercially available product (for example, SI-30 manufactured by Catalysts and Chemicals Industries Co., Ltd.) may be used as long as the product contains silica-based fine particles having an average particle size of 2 to 300 nm. The concentration of the silica-based fine particles contained in the silica sol is preferably in the range from 0.5 to 5% by weight.

The aqueous solution of the silicic acid solution (hereinafter sometimes referred to simply as a "silicic acid solution") used in the above step (2) is obtained, for example, by treating an aqueous solution of a silicate, for example, an alkali metal silicate such as sodium silicate (water glass) or potassium silicate, or an organic base silicate such as quaternary ammonium silicate, with a cation-exchange resin to remove alkali cations.

It is preferable to use, among these aqueous solutions of the silicic acid solution, an aqueous solution having a pH of 2 to 4 and a silicon content of 0.5 to 5% by weight in terms of $SiO_2$.

It is preferable that the mixed aqueous solution-(1) obtained in the above step (1) and the silicic acid solution be prepared respectively so that the molar ratio ($ZrO_2/SiO_2$-(1)) is 1/16 to 1/1, when the zirconium components in the mixed aqueous solution-(1) are expressed as $ZrO_2$ and the silicon components contained in the silicic acid solution are expressed as $SiO_2$-(1), and that they be added together slowly into the silica sol.

It is also preferable that the amount of these solutions to be added to the silica sol be in the range of 7/100 to 15/10 in terms of weight ratio $\{(ZrO_2/SiO_2\text{-}(1))/SiO_2\text{-}(2)\}$, when the silica-based fine particles are expressed as $SiO_2$-(2), although the amount to be added varies depending on the degree of coating of the silica-based fine particles contained in the silica sol. Preferably, the silica sol is heated previously to a temperature of 70 to 95° C. before these solutions are added.

When the mixed aqueous solution-(1) and the aqueous solution of the silicic acid solution are added under stirring to the silica sol, as described above, the zirconium components and the silicon components undergo hydrolysis reactions in the mixed aqueous solution-(2), and the surfaces of the silica-based fine particles contained in the silica sol are covered with coatings of partial hydrolysates or hydrolysates of the above components.

As the mixed aqueous solution-(1) having strong alkalinity is added to the silica sol, the pH of the mixed aqueous solution-(2) increases with time. Therefore, it is desirable to stop the addition of the mixed aqueous solution-(1) and the silicic acid solution when the pH of the mixed aqueous solution-(2) approaches 11. When the pH exceeds 11, the silica-based fine particles contained in the silica sol begin to be dissolved in the mixed aqueous solution-(2) due to the alkalinity, which is not preferable.

Therefore, if the addition of the mixed aqueous solution-(2) and the silicic acid solution has not yet been completed at the time when the pH reaches 11, it is preferable that the step (3) as described below be performed to remove alkali cations, and then the operation of the step (2) be carried out again or be repeated.

In the step (3), the mixed aqueous solution-(2) obtained in the step (2) is subjected to a treatment with a cation-exchange resin to remove alkali cations. There is no particular limitation on the cation-exchange resin used in this step. It is preferable to use a cation-exchange resin such as SK1BH manufactured by Mitsubishi Chemical Corporation.

In this step, it is preferable that the mixed aqueous solution-(2) be subjected to the above treatment for removing alkali cations so that the mixed aqueous solution-(2) has a pH of 7.0 to 10.0.

In the above step (4), the mixed aqueous solution-(3) obtained in the step (3) is subjected to a hydrothermal treatment in a reaction vessel at a temperature of 100° C. to 350° C. The reaction vessel is not particularly limited as long as it is a pressure and heat resistant vessel capable of withstanding a pressure of 0.5 to 16.5 MPa, and a stainless steel autoclave is used preferably.

Thus, a mixed aqueous solution-(4) containing the amorphous powder (B) in which the surfaces of the silica-based fine particles are covered with coatings of an oxide containing at least a zirconium atom, a silicon atom, and an oxygen atom is obtained.

In the step (5), the solid product composed of the amorphous powder (B) contained in the mixed aqueous solution-(4) obtained in the step (4) is dried. The solid product contained in the mixed aqueous solution-(4) can be dried by being subjected to a commonly used conventional drying step, for example, a step of filtering the solid product from the mixed aqueous solution-(4), washing the filtered solid product with pure water or distilled water if necessary, and then drying the washed solid product by hot air at a temperature of 80 to 250° C.

It is desirable to subject the dried product obtained in this hot air drying step to a grinding step using a mortar and a ball mill, if necessary, to adjust the particle size. The resulting dried product has a partial structure, as shown in FIG. 1, for example, in which the oxide coating of a silica-based fine particle and the oxide coating of a neighboring silica-based fine particle extend and are connected to each other, and the oxide coatings each cover a plurality of silica-based fine particles. The resulting dried product has, as an overall structure, a porous particle structure, as shown in FIG. 2, for example, in which the oxide coatings are connected to each other to form an aggregate of the silica-based fine particles covered with the oxide coatings.

In the above step (5), the amorphous powder (B) of nearly spherical or spherical particles in overall shape can be obtained also by spray-drying the mixed aqueous solution-(4) (with a spray dryer or the like).

Thus, a dried amorphous powder or a ground product thereof consisting of inorganic oxide fine particles including silica-based fine particles covered with coatings of an oxide containing at least zirconium, silicon, and oxygen is obtained.

The dried amorphous powder or the ground product thereof obtained as above may be used as it is as the amorphous powder (B) used in the present invention, but it is preferable that the dried amorphous powder or the ground product thereof be calcined at a temperature of 300 to 900° C. in terms of the mechanical strength and wear resistance. A known method can be used for the calcining without any limitation. Preferably, the dried amorphous powder or the ground product thereof is calcined in a quartz crucible placed in an electric furnace.

The calcined product of the amorphous powder (B) (calcined amorphous powder) can be obtained easily by calcining the dried amorphous powder in the manner as described above. The shape of the particles of the calcined product is almost the same as that of the particles of the above-mentioned dried amorphous powder, although some of the particles are contracted.

Accordingly, the calcined product of the amorphous powder (B) also can have a porous particle structure in which the oxide coatings are connected to each other to form an aggregate of the silica-based fine particles covered with the oxide coatings. The calcined product obtained in the calcining step may be subjected to the grinding step using a mortar, a ball mill, etc., if necessary, to adjust the particle size.

In the dental composition of the present invention, the absolute value of the difference in refractive index between the cured product of the polymerizable monomer (A) and the amorphous powder (B) is 0.005 to 0.03. If the above-mentioned surface treatment layer is formed on the amorphous powder (B), the refractive index of the amorphous powder (B) is a value of the refractive index of the powder without the surface treatment layer. That is, the refractive index of the amorphous powder (B), which has not been subjected to the surface treatment, is used as a reference.

Generally, the light diffusion property of the cured product of a dental composition tends to decrease as its transparency increases, and it is difficult to obtain a dental composition capable of achieving a good balance between the transparency and the light diffusion property as a cured product. Even if a dental composition achieves a good balance between the transparency and the light diffusion property, such a composition has a drawback of impairing other properties required therefor. As a result of intensive studies, the present inventors have found that the use of the amorphous powder (B), in which the silica-based fine particles are covered with coatings of an oxide containing a zirconium atom, a silicon atom, and an oxygen atom, allows the refractive index of the filler component to be increased, while providing good mechanical strength and surface smoothness and gloss after polishing to the cured product of the dental composition, and good handling properties to the paste thereof, and furthermore that, when a special filler like this amorphous powder (B) is used in combination with the polymerizable monomer (A) so that the difference in refractive index between them falls within the above-mentioned range of values, the resulting dental composition can achieve a good balance between the excellent transparency and light diffusion property.

The light diffusion property is a property of diffusing light in various directions by light refraction and reflection on fillers contained in a translucent material like a dental composite material when the light enters into the material. The reflected and diffused light observed has a color tone that reflects the color of the dental composite material and its background color. Presumably, the higher the light diffusion property is, the more a background color of a restored part is blurred or the more the boundary between a restored part and natural teeth is blurred, and the color matching with the natural teeth is increased accordingly. A proposed measure of the light diffusion property is a degree of diffusion D defined by the following formula (1):

$$D=(I_{20}/\cos 20°+I_{70}/\cos 70°)/(2I_0) \tag{1}$$

where I denotes the intensity of transmitted light through a sample, and $I_0$, $I_{20}$ and $I_{70}$ denote the intensities (the intensities of light) of the transmitted light measured at angles of 0, 20, and 70 degrees respectively with respect to the direction perpendicular to the sample plate (the incident direction of the light).

The luminous intensities (the intensities of light) can be measured with a variable-angle photometer or a goniophotometer. A higher value of the degree of diffusion D means a higher level of the light diffusion property of a cured product.

According to the dental composition of the present invention, the degree of diffusion D of 0.01 to 0.5 can be achieved. When the degree of diffusion D has a value smaller than 0.01, the light diffusion property of the dental composition is insufficient and the composition does not match natural teeth so well. When the degree of diffusion D has a value greater than 0.5, the light diffusion property of the dental composition is excessively high and sufficient transparency cannot be obtained. Therefore, it can be said that the dental composition of the present invention has a high light diffusion property that provides a good match with natural teeth. Preferably, the degree of diffusion D has a value of 0.02 to 0.4, and more preferably 0.03 to 0.3, in terms of matching with natural teeth. In the dental composition of the present invention, the above-described difference in the refractive index can be adjusted to obtain a preferable range of degrees of diffusion D. The degree of diffusion D tends to decrease as the difference in the refractive index decreases.

A proposed measure of transparency is a degree of transparency ΔL represented by the following formula (2):

$$\Delta L = Lw - Lb \quad (2)$$

where Lw denotes the brightness of a sample when measured on a standard white plate, and Lb denotes the brightness of the sample when measured on a standard black plate.

The degree of transparency (ΔL) can be obtained by measuring the brightness (Lw) of a sample on a standard white plate placed behind the sample and the brightness (Lb) of the same sample on a standard black plate placed behind the sample, using a spectrophotometer (CM-3610d manufactured by Minolta Co., Ltd.) equipped with an illuminant C light source with a 2° observer. A higher value of the degree of transparency ΔL means a higher level of the transparency of a cured product.

According to the dental composition of the present invention, the degree of transparency ΔL of 30 to 50 can be achieved. When the degree of transparency ΔL has a value smaller than 30, the dental composition has insufficient transparency and has a texture different from natural teeth. When the degree of transparency has a value greater than 50, the dental composition has an insufficient light diffusion property and does not match natural teeth so well. Therefore, it can be said that the dental composition of the present invention has high transparency that provides a good match with natural teeth. More preferably, the degree of transparency ΔL has a value of 35 to 50, and particularly preferably 40 to 50. In the dental composition of the present invention, the above-described difference in the refractive index can be adjusted to obtain a preferable range of degrees of transparency ΔL. The degree of transparency ΔL tends to increase as the difference in the refractive index decreases.

Next, in order to further enhance the performance of the dental composition of the present invention, components such as inorganic particles (C), inorganic ultrafine particles (D), and a polymerization initiator (E) may be contained therein as long as they do not impair the advantageous effects of the present invention.

The dental composition of the present invention may contain the inorganic particles (C) to enhance the mechanical properties, etc. of the cured product thereof. As the inorganic particles (C), any known inorganic particles used in dental compositions are used without any limitation. Examples of the inorganic particles include: various kinds of glass powders [containing silica as a main component and further containing an oxide of a heavy metal, boron, aluminum, and the like, if necessary: e.g., glass powders having typical compositions, such as fused silica, quartz, soda lime silica glass, E-glass, C-glass, borosilicate glass (Pyrex (registered trademark) glass); and glass powders for dental use, such as barium glass (GM 27884 and 8235 manufactured by Schott, and Ray-Sorb E-2000 and Ray-Sorb E-3000 manufactured by Specialty Glass), strontium borosilicate glass (Ray-Sorb E-4000 manufactured by Specialty Glass), lanthanum glass ceramics (GM 31684 manufactured by Schott), and fluoroaluminosilicate glass (GM 35429, G018-091, G018-117 manufactured by Schott)]; various kinds of ceramics; composite oxides such as silica-titania, and silica-zirconia; diatomaceous earth; kaolin; clay minerals (such as montmorillonite); activated white clay; synthetic zeolite; mica; calcium fluoride; ytterbium fluoride; yttrium fluoride; calcium phosphate; barium sulfate; zirconium dioxide; titanium dioxide; hydroxyapatite; and the like. Any one of the above-mentioned inorganic particles can be used alone or as a mixture of two or more kinds thereof. Among them, those containing silica as a main component (at least 25% by weight of silica, preferably at least 40% by weight of silica) are used suitably.

The average particle size of the inorganic particles (C) is preferably 0.1 to 1.0 μm, more preferably 0.2 to 0.9 μm, and particularly preferably 0.4 to 0.7 μm. When the average particle size is less than 0.1 μm, the mechanical strength may be insufficient, or the paste becomes sticky, which may cause insufficient handling properties. When the average particle size exceeds 1.0 μm, the surface smoothness and gloss after polishing and the gloss durability as a cured product may be impaired. The average particle size of the inorganic particles (C) can be measured in the same manner as the average particle size of the amorphous powder (B) described above.

Like the amorphous powder (B), the inorganic particles (C) are used in combination with a polymerizable monomer for the dental composition. Therefore, it is desirable that the inorganic particles (C) be subjected previously to surface treatment with a surface treating agent to improve the affinity between the inorganic filler and the polymerizable monomer, and to increase the chemical bonding between the inorganic filler and the polymerizable monomer so as to enhance the mechanical strength of the cured product. As such a surface treating agent, any one of the organic metal compounds described as examples for the amorphous powder (B) can be used likewise.

The shape of the inorganic particles (C) is not particularly limited. The inorganic particles (C) can be used as an irregular-shaped or spherical powder particles. If the irregular-shaped inorganic particles (B) are used, the mechanical strength and wear resistance are particularly excellent, and if the spherical inorganic particles (C) are used, the surface smoothness and gloss after polishing and the gloss durability are particularly excellent. The shape of the inorganic particles (C) may be selected suitably in accordance with the intended use of the dental composition.

The refractive index of the inorganic particles (C) is not particularly limited. For ease of approximation to the refractive indices of the cured product of the above-described polymerizable monomer (A) and the amorphous powder (B), the refractive index of the inorganic particles (C) is preferably 1.45 to 1.65, more preferably 1.50 to 1.60, and particularly preferably 1.52 to 1.58. It is desirable that the difference in refractive index from the cured product of the polymerizable monomer (A) and the amorphous powder (B) be as small as possible.

The amount of the inorganic particles (C) to be added is preferably 50 to 400 parts by weight per 100 parts by weight of the polymerizable monomer (A), more preferably 100 to 350 parts by weight, and particularly preferably 150 to 300 parts by weight.

The dental composition of the present invention may contain the inorganic ultrafine particles (D) to enhance the handling properties thereof as a paste. As the inorganic ultrafine particles (D) in the present invention, any known inorganic ultrafine particles used in dental compositions are used without any limitation. Preferable examples of the inorganic ultrafine particles (D) include particles of inorganic oxides such as silica, alumina, titania, zirconia, particles of composite oxides of any of these oxides, and particles of calcium phosphate, hydroxyapatite, yttrium fluoride, ytterbium fluoride, and the like. Preferably, the inorganic ultrafine particles (D) are particles of silica, alumina, titania, or the like prepared by flame pyrolysis, and examples thereof include products manufactured by Japan Aerosil Co., Ltd. under the trade names of Aerosil, Aeroxide Alu C, Aeroxide $TiO_2$ P 25, Aeroxide $TiO_2$ P 25S, VP Zirconium Oxide 3-YSZ, and VP Zirconium Oxide 3-YSZ PH.

The average particle size of the inorganic ultrafine particles (D) is preferably 5 to 50 nm, and more preferably 10 to 40 nm. The average particle size of the inorganic ultrafine particles (D) can be measured by taking electron micrographs of these ultrafine particles (D) and calculating the average value of the diameters of the 100 randomly-selected ultrafine particles. If the ultrafine particles are non-spherical particles, their diameters are obtained by calculating the arithmetic average of the longest and shortest dimensions thereof. If the ultrafine particles are aggregated particles, their average particle size is the average particle size of the primary particles.

Like the amorphous powder (B), the inorganic ultrafine particles (D) are used in combination with a polymerizable monomer for the dental composition. Therefore, it is desirable that the inorganic ultrafine particles (D) be subjected previously to surface treatment with a surface treating agent to improve the affinity between the inorganic filler and the polymerizable monomer, and to increase the chemical bonding between the inorganic filler and the polymerizable monomer so as to enhance the mechanical strength of the cured product. As the surface treating agent, any one of the organic metal compounds described as examples for the amorphous powder (B) can be used likewise.

The amount of the inorganic ultrafine particles (D) to be added is preferably 10 to 50 parts by weight per 100 parts by weight of the polymerizable monomer (A), more preferably 10 to 40 parts by weight, and particularly preferably 15 to 30 parts by weight.

It is preferable that the dental composition of the present invention contain the polymerization initiator (E) to facilitate polymerization and curing. The polymerization initiator (E) can be selected from polymerization initiators commonly used in the industrial field. Among them, polymerization initiators used for dental applications are used preferably. Particularly, photopolymerization initiators and chemical polymerization initiators are used alone, or two or more of them are used in suitable combination.

Examples of the photopolymerization initiator include (bis)acylphosphine oxides, water-soluble acylphosphine oxides, thioxanthones or quaternary ammonium salts of thioxanthones, ketals, α-diketones, benzoin alkyl ether compounds, and α-amino ketone compounds.

Among (bis)acylphosphine oxides used as the photopolymerization initiator, examples of the acylphosphine oxides include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, and benzoyl di-(2,6-dimethylphenyl)phosphonate. Examples of the bisacylphosphine oxides include bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis-(2,6-dimethoxybenzoyl)phenylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide, and (2,5,6-trimethylbenzoyl)-2,4,4-trimethylpentylphosphine oxide.

Preferably, the water-soluble acylphosphine oxides used as the photopolymerization initiator have alkali metal ions, alkaline earth metal ions, pyridinium ions, or ammonium ions in the acylphosphine oxide molecules. For instance, the water-soluble acylphosphine oxides can be synthesized by the method disclosed in EP 0009348 B1 or JP 57(1982)-197289 A.

Specific examples of the aforementioned water-soluble acylphosphine oxides include sodium monomethylacetylphosphonate, sodium monomethyl(1-oxopropyl)phosphonate, sodium monomethylbenzoylphosphonate, sodium monomethyl(1-oxobutyl)phosphonate, sodium monomethyl(2-methyl-1-oxopropyl)phosphonate, sodium acetylphosphonate, sodium monomethylacetylphosphonate, sodium acetylmethylphosphonate, methyl-4-(hydroxymethoxyphosphinyl)-4-oxobutanoate sodium salt, methyl-4-oxophosphonobutanoate monosodium salt, acetylphenylphosphinate sodium salt, sodium (1-oxopropyl)pentylphosphinate, methyl-4-(hydroxypentylphosphinyl)-4-oxobutanoate sodium salt, sodium acetylpentylphosphinate, sodium acetylethylphosphinate, sodium methyl(1,1-dimethyl)methylphosphinate, sodium (1,1-diethoxyethyl)methylphosphinate, sodium (1,1-diethoxyethyl)methylphosphinate, methyl-4-(hydroxymethylphosphinyl)-4-oxobutanoate lithium salt, 4-(hydroxymethylphosphinyl)-4-oxobutanoic acid dilithium salt, methyl(2-methyl-1,3-dioxolan-2-yl)phosphinate sodium salt, methyl(2-methyl-1,3-thiazolidin-2-yl)phosphonite sodium salt, (2-methylperhydro-1,3-diazin-2-yl)phosphonite sodium salt, acetylphosphinate sodium salt, (1,1-diethoxyethyl)phosphonite sodium salt, (1,1-diethoxyethyl)methylphosphonite sodium salt, methyl(2-methyloxathiolane-2-yl)phosphinate sodium salt, methyl(2,4,5-trimethyl-1,3-dioxolan-2-yl)phosphinate sodium salt, methyl(1,1-propoxyethyl)phosphinate sodium salt, (1-methoxyvinyl)methylphosphinate sodium salt, (1-ethylthiovinyl)methylphosphinate sodium salt, methyl(2-methylperhydro-1,3-diazin-2-yl)phosphinate sodium salt, methyl(2-methylperhydro-1,3-thiazin-2-yl)phosphinate sodium salt, methyl(2-methyl-1,3-diazolidin-2-yl)phosphinate sodium salt, methyl(2-methyl-1,3-thiazolidin-2-yl)phosphinate sodium salt, (2,2-dicyano-1-methylethynyl)phosphinate sodium salt, acetylmethylphosphinate oxime sodium salt, acetylmethylphosphinate-O-benzyloxime sodium salt, 1-[(N-ethoxyimino)ethyl]methylphosphinate sodium salt, methyl(1-phenyliminoethyl)phosphinate sodium salt, methyl (1-phenylhydrazone ethyl)phosphinate sodium salt, [1-(2,4-dinitrophenylhydrazono)ethyl]methylphosphinate sodium salt, acetylmethylphosphinate semicarbazone sodium salt, (1-cyano-1-hydroxyethyl)methylphosphinate sodium salt, (dimethoxymethyl)methyl phosphinate sodium salt, formylmethylphosphinate sodium salt, (1,1-dimethoxypropyl)methylphosphinate sodium salt, methyl(1-oxopropyl)phosphinate sodium salt, dodecylguanidine salt of (1,1-dimethoxypropyl)methylphosphinate, isopropylamine salt of (1,1-dimethoxypropyl)methylphosphinate, acetylmethylphosphinate thiosemicarbazone sodium salt, 1,3,5-tributyl-4-methylamino-1,2,4-triazolium (1,1-dimethoxyethyl)-methylphosphinate, 1-butyl-4-butylaminomethylamino-3,5-dipropyl-1,2,4-triazolium (1,1-dimethoxyethyl)-methylphosphinate, 2,4,6-trimethylbenzoylphenylphosphine oxide sodium salt, 2,4,6-trimethylbenzoylphenylphosphine oxide potassium salt, and ammonium salt of 2,4,6-trimethylbenzoylphenylphosphine oxide. Furthermore, examples thereof also include compounds described in JP 2000-159621 A.

Among these (bis)acylphosphine oxides and water-soluble acylphosphine oxides, particularly preferable ones are 2,4,6-trimethylbenzoyldiphenylphosphine oxide, 2,4,6-trimethylbenzoylmethoxyphenylphosphine oxide, bis(2,4,6-trimethylbenzoyl)phenylphosphine oxide, and 2,4,6-trimethylbenzoylphenylphosphine oxide sodium salt.

Examples of thioxanthones or the quaternary ammonium salts of thioxanthones that are used as the above-mentioned photopolymerization initiators include thioxanthone, 2-chlorothioxanthen-9-one, 2-hydroxy-3-(9-oxy-9H-thioxanthen-4-yloxy)-N,N,N-trimethyl-propaneaminium chloride, 2-hydroxy-3-(1-methyl-9-oxy-9H-thioxanthen-4-yloxy)-N,N,N-trimethyl-propaneaminium chloride, 2-hydroxy-3-(9-oxo-9H-thioxanthen-2-yloxy)-N,N,N-trimethyl-propaneaminium chloride, 2-hydroxy-3-(3,4-dimethyl-9-oxo-9H-thioxanthen-2-yloxy)-N,N,N-trimethyl-1-propaneaminium chloride, 2-hydroxy-3-(3,4-dimethyl-9H-thioxanthen-2-yloxy)-N,N,N-trimethyl-1-propaneaminium chloride, and 2-hydroxy-3-(1,3,4-trimethyl-9-oxo-9H-thioxanthen-2-yloxy)-N,N,N-trimethyl-1-propaneaminium chloride.

Among the thioxanthones or the quaternary ammonium salts of thioxanthones, a particularly preferable thioxanthone is 2-chlorothioxanthen-9-one, and a particularly preferable quaternary ammonium salt of thioxanthone is 2-hydroxy-3-(3,4-dimethyl-9H-thioxanthen-2-yloxy)-N,N,N-trimethyl-1-propaneaminium chloride.

Examples of ketals used as the photopolymerization initiator include benzyl dimethyl ketal and benzyl diethyl ketal.

Examples of the α-diketones used as the photopolymerization initiator include diacetyl, dibenzyl, camphorquinone, 2,3-pentadione, 2,3-octadione, 9,10-phenanthrenequinone, 4,4'-oxybenzyl, and acenaphthenequinone. Among these, camphorquinone is particularly preferable from the viewpoint of having the maximum absorption wavelength in the visible light range.

Examples of the benzoin alkyl ethers used as the aforementioned photopolymerization initiator include benzoin methyl ether, benzoin ethyl ether, benzoin isopropyl ether, and benzoin isobutyl ether.

Examples of the α-aminoketones used as the aforementioned photopolymerization initiator include 2-methyl-1-[4-(methylthio)phenyl]-2-morpholinopropan-1-one.

Preferably, among these photopolymerization initiators, at least one selected from the group consisting of (bis)acylphosphine oxides, salts thereof, and α-diketones is used. This makes it possible to obtain a composition that has excellent photocurability in visible and near-ultraviolet ranges and sufficiently high photocurability regardless of which light source among a halogen lamp, light-emitting diode (LED), and xenon lamp is used.

Among the polymerization initiators (E) used in the present invention, a chemical polymerization initiator that is used preferably is organic peroxide. The organic peroxide used as the chemical polymerization initiator is not particularly limited and a known one can be used. Examples of typical organic peroxides include ketone peroxide, hydroperoxide, diacyl peroxide, dialkyl peroxide, peroxyketal, peroxyester, and peroxydicarbonate.

Examples of the ketone peroxide used as the chemical polymerization initiator include methyl ethyl ketone peroxide, methyl isobutyl ketone peroxide, methylcyclohexanone peroxide, and cyclohexanone peroxide.

Examples of the hydroperoxide used as the chemical polymerization initiator include 2,5-dimethylhexane-2,5-dihydroperoxide, diisopropylbenzene hydroperoxide, cumene hydroperoxide, and t-butyl hydroperoxide.

Examples of the diacyl peroxide used as the chemical polymerization initiator include acetyl peroxide, isobutyryl peroxide, benzoyl peroxide, decanoyl peroxide, 3,5,5-trimethylhexanoyl peroxide, 2,4-dichlorobenzoyl peroxide, and lauroyl peroxide.

Examples of the dialkyl peroxide used as the chemical polymerization initiator include di-t-butyl peroxide, dicumyl peroxide, t-butylcumyl peroxide, 2,5-dimethyl-2,5-di(t-butylperoxy)hexane, 1,3-bis(t-butylperoxyisopropyl)benzene, and 2,5-dimethyl-2,5-di(t-butylperoxy)-3-hexyne.

Examples of the peroxyketal used as the chemical polymerization initiator include 1,1-bis-butylperoxy)-3,3,5-trimethylcyclohexane, 1,1-bis-butylperoxy)cyclohexane, 2,2-bis(t-butylperoxy)butane, 2,2-bis(t-butylperoxy)octane, and 4,4-bis(t-butylperoxy)valeric acid-n-butyl ester.

Examples of the peroxyester used as the chemical polymerization initiator include α-cumyl peroxyneodecanoate, t-butyl peroxyneodecanoate, t-butyl peroxypivarate, 2,2,4-trimethylpentylperoxy-2-ethyl hexanoate, t-amylperoxy-2-ethyl hexanoate, t-butylperoxy-2-ethyl hexanoate, di-t-butylperoxy isophthalate, di-t-butylperoxy hexahydroterephthalate, t-butylperoxy-3,3,5-trimethyl hexanoate, t-butylperoxy acetate, t-butylperoxy benzoate, and t-butylperoxymaleic acid.

Examples of the peroxydicarbonate used as the chemical polymerization initiator include di-3-methoxy peroxydicarbonate, di-2-ethylhexyl peroxydicarbonate, bis(4-t-butylcyclohexyl)peroxydicarbonate, diisopropyl peroxydicarbonate, di-n-propyl peroxydicarbonate, di-2-ethoxyethyl peroxydicarbonate, and diallyl peroxydicarbonate.

Among these organic peroxides, diacyl peroxides are used preferably from the viewpoint of a comprehensive balance of safety, storage stability, and radical production ability, and among these, benzoyl peroxide is used particularly preferably.

The amount of the polymerization initiator (E) to be added in the present invention is not particularly limited. However, from the viewpoint of, for example, curability of the resultant composition, it is preferable that 0.01 to 10 parts by weight of the polymerization initiator (E) be contained per 100 parts by weight of the polymerizable monomer (A), and it is more preferable that 0.1 to 5 parts by weight of the polymerization initiator (E) be contained. When the amount of the polymerization initiator (E) is less than 0.01 part by weight, polymerization may not proceed sufficiently and thereby mechanical strength may be reduced. Therefore, the amount is more preferably at least 0.1 part by weight. On the other hand, when the amount of the polymerization initiator (E) exceeds 10 parts by weight, in the case where the polymerization initiator itself has low polymerization performance, sufficient mechanical strength may not be obtained and furthermore precipitation from the composition may occur. Therefore, the amount is more preferably 5 parts by weight or less.

In a preferred embodiment, a polymerization accelerator is used. Examples of the polymerization accelerator used in the present invention include amines, sulfinic acids and salts thereof, aldehydes, and thiol compounds.

Amines used as the polymerization accelerator can be divided into aliphatic amines and aromatic amines. Examples of aliphatic amines include: primary aliphatic amines such as n-butylamine, n-hexylamine, and n-octylamine; secondary aliphatic amines such as diisopropylamine, dibutylamine, and N-methylethanolamine; and tertiary aliphatic amines such as N-methyldiethanolamine, N-ethyldiethanolamine, N-n-butyldiethanolamine, N-lauryldiethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, triethanolamine, trimethylamine, triethylamine, and tributylamine. Among these, tertiary aliphatic amines are preferable from the viewpoint of curability and storage stability of the composition, and particularly, N-methyldiethanolamine and triethanolamine are used more preferably.

Examples of aromatic amines include N,N-bis(2-hydroxyethyl)-3,5-dimethylaniline, N,N-di(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-diisopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, 4-N,N-dimethylaminobenzoic acid ethyl ester, 4-N,N-dimethylaminobenzoic acid methyl ester, N,N-dimethylaminobenzoic acid n-butoxyethyl ester, 4-N,N-dimethylaminobenzoic acid 2-(methacryloyloxy)ethyl ester, 4-N,N-dimethylaminobenzophenone, and butyl 4-dimethylaminobenzoate. Among these, at least one selected from the group consisting of N,N-di(2-hydroxyethyl)-p-toluidine, 4-N,N-dimethylaminobenzoic acid ethyl ester, N,N-dimethylaminobenzoic acid n-butoxyethyl ester, and 4-N,N-dimethylaminobenzophenone is used preferably from the viewpoint of being capable of providing the composition with excellent curability.

Examples of the sulfinic acid or salt thereof used as the polymerization accelerator include p-toluenesulfinic acid, sodium p-toluenesulfinate, potassium p-toluenesulfinate, lithium p-toluenesulfinate, calcium p-toluenesulfinate, benzenesulfinic acid, sodium benzenesulfinate, potassium benzenesulfinate, lithium benzenesulfinate, calcium benzenesulfinate, 2,4,6-trimethylbenzenesulfinic acid, sodium 2,4,6-trimethylbenzenesulfinate, potassium 2,4,6-trimethylbenzenesulfinate, lithium 2,4,6-trimethylbenzenesulfinate, calcium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, lithium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, lithium 2,4,6-triisopropylbenzenesulfinate, and calcium 2,4,6-triisopropylbenzenesulfinate. Sodium benzenesulfinate, sodium p-toluenesulfinate, and sodium 2,4,6-triisopropylbenzenesulfinate are particularly preferable.

Examples of aldehydes used as the polymerization accelerator include derivatives of terephthalaldehyde and benzaldehyde. Examples of the benzaldehyde derivative include dimethylaminobenzaldehyde, p-methyloxybenzaldehyde, p-ethyloxybenzaldehyde, and p-n-octyloxybenzaldehyde. Among these, from the viewpoint of curability, p-n-octyloxybenzaldehyde is used preferably.

Examples of the thiol compound used as the polymerization accelerator include 3-mercaptopropyltrimethoxysilane, 2-mercaptobenzoxazole, decanethiol, and thiobenzoic acid.

The amount of polymerization accelerator to be added in the present invention is not particularly limited. However, from the viewpoints of, for example, curability of the resultant composition, it is preferable that 0.001 to 10 parts by weight of polymerization accelerator be contained per 100 parts by weight of the polymerizable monomer component (A), and it is more preferable that 0.001 to 5 parts by weight of the polymerization accelerator be contained. When the amount of the polymerization accelerator is less than 0.001 part by weight, polymerization may not proceed sufficiently and mechanical strength may be reduced. Therefore, the amount is more preferably at least 0.05 part by weight. On the other hand, when the amount of the polymerization accelerator exceeds 10 parts by weight, in the case where the polymerization initiator itself has low polymerization performance, sufficiently high mechanical strength may not be obtained. Therefore, the amount is more preferably 5 parts by weight or less.

To the dental composition of the present invention, a pH adjuster, an ultraviolet absorber, an antioxidant, a polymerization inhibitor, a colorant, an antibacterial agent, an X-ray contrast agent, a thickening agent, a fluorescent agent, or the like can further be added in accordance with the intended use.

For example, when the cured surface is expected to have a fluorine ion sustained-release property, a fluorine ion sustained-releasable filler, such as fluoroaluminosilicate glass, calcium fluoride, sodium fluoride, or sodium monofluorophosphate also can be added.

When it is expected to have an antibacterial property, for example, a surfactant having an antibacterial activity, such as cetylpyridinium chloride or 12-(meth)acryloyloxydodecylpyridinium bromide, or a photocatalytic titanium oxide can be added.

According to the dental composition of the present invention, the dental composition has an excellent light diffusion property and high transparency, and therefore, a cured product that matches natural teeth so well can be obtained. In addition, the cured product has high surface smoothness and gloss after polishing, and therefore, the dental material using the dental composition of the present invention has a good aesthetic appearance. Further, the dental composition of the present invention has high mechanical strength as a cured product, and the mechanical strength can be enhanced further by the addition of the inorganic particles (C). Furthermore, the dental composition of the present invention has good handling properties as well as proper fluidity and forming property as a paste, and the adhesion to dental instruments and stickiness are reduced. That is, the dental composition is very easy to handle.

The dental composition of the present invention can be used suitably in a conventional manner as dental materials, for example, dental composite resins such as dental composite filling materials, dental crown materials, and luting materials, dental adhesives such as orthodontic adhesives, cavity coating adhesives, and dental fissure sealing materials, denture base materials, tissue conditioning materials for denture bases, fissure sealants, coating materials applied to tooth surfaces and dental prostheses, surface glazing materials, and dental lacquers. The cured product obtained by polymerizing and curing the dental composition of the present invention also can be molded to be used as artificial teeth, dentures, and resin blocks for CAD/CAM. Among them, the dental composition of the present invention can be used advantageously as a dental composite resin. This composite resin exhibits both a high light diffusion property and high transparency and matches natural teeth very well, and has good mechanical strength, and surface smoothness and gloss after polishing as a cured product as well as good handling properties as a paste.

The present invention will be described in more detail below by the following examples, without intending to limit the scope of the present invention to these examples. The test methods, materials, etc. used in the examples are shown below.

[Measurement of Particle Size of Powder]

A laser diffraction particle size distribution analyzer (SALD-2100 manufactured by Shimadzu Corporation) was used to measure the particle size of each of the produced powders. As a dispersion medium, a 0.2% aqueous solution of sodium hexametaphosphate was used.

[Refractive Index]

The refractive index of each of the produced powders was measured with an Abbe's refractometer by the immersion method, in which a sodium D-line was used as a light source, and diiodomethane in which sulfur is dissolved, 1-bromonaphthalene, methyl salicylate, dimethylformamide, 1-pentanol, or the like was used as a liquid. To measure the refractive index of each of the polymers of the polymerizable monomers (A) used in Examples and Comparative Examples, a test sample prepared in the following manner was used. 0.5 part by weight of α-camphorquinone as a polymerization initiator and 1.0 part by weight of ethyl N,N-dimethylaminobenzoate as a polymerization accelerator were dissolved in 100 parts by weight of the polymerizable monomer (A), and the resulting mixture was degassed and then photopolymerized to obtain a cured product. Then, the cured product was formed into a rectangular parallelepiped of 5 mm×10 mm×20 mm as a test sample.

[Transparency of Cured Product]

A disk-shaped test sample (20 mmφ×1.0 mm) of the cured product of the dental composition was prepared. The brightness (Lw) of the test sample on a standard white plate placed behind the sample and the brightness (Lb) of the same test sample on a standard black plate placed behind the sample were measured using a spectrophotometer (CM-3610d manufactured by Minolta Co., Ltd.) equipped with an illuminant C light source with a 2° observer, and the difference between the brightness (Lw) and the brightness (Lb) (ΔL=Lw−Lb) was calculated to be used as a measure of the degree of transparency. A higher value of ΔL means a higher level of the transparency of the cured product.

[Measurement of Degree of Diffusion]

The produced dental composition was filled in a Teflon (registered trademark) mold (with a diameter of 30 mm×a thickness of 0.3 mm). The mold was clamped between upper and lower glass slides, and the upper and lower surfaces of the mold were each exposed to light irradiation for 1 minute. Thus, the dental composition was cured. The cured product was taken out of the mold, and then the luminous intensity distribution of transmitted light was measured with a three-dimensional multi-angle photometer (GP-200, manufactured by Murakami Color Research Laboratory Co., Ltd.). The degree of diffusion D was calculated according to the above formula (1).

[Handling Properties]

The dental composition was filled in a cavity of 4 mmφ×4 mm, and the handling properties of the composition as a paste were evaluated, in terms of ease of filling, according to the following evaluation criteria.

<Evaluation Criteria of Handling Properties>

A: Neither stickiness nor dryness observed. Excellent in filling handling properties.
B: Slightly sticky or slightly dry. Easy to fill.
C: Very sticky or very dry. Difficult to fill.

The pastes rated A and B are suitable for practical use.

[Flexural Strength of Cured Product]

A test sample (2 mm×2 mm×30 mm) of the cured product of the produced dental composition was prepared. The test sample was immersed in water at 37° C. for 24 hours. The flexural strength of the test sample was measured using a universal testing machine (manufactured by Instron) with the span being set at 20 mm and the crosshead speed being set at 1 mm/min according to a three-point flexural test method.

[Polishability]

The produced dental composition was filled in a stainless steel mold (with a thickness of 1 mm and a diameter of 15 mm). The mold was clamped between upper and lower glass slides and the upper and lower surfaces of the mold were each exposed to light irradiation for 2 minutes. Thus, the dental composition was cured. The cured product was taken out of the mold, and then one surface of the cured product was polished with a #800 waterproof abrasive paper. Then, this polished surface was buffed with a dental polishing kit (EWL 80, manufactured by KAVO) at 3000 rpm for 20 seconds. As a polishing material, Porceny Hydron (manufactured by Tokyo Shizaisha) was used. The gloss of the polished surface was measured with a glossmeter (VG-107, manufactured by Nippon Denshoku Industries Co., Ltd.) and indicated as a ratio to the specular gloss of 100%. The measurement was performed at an angle of 60 degrees.

PREPARATION EXAMPLE 1

Preparation of Polymerizable Monomer A-1

0.5 parts by weight of α-camphorquinone as a polymerization initiator and 1.0 part by weight of ethyl N,N-dimethylaminobenzoate as a polymerization accelerator were dissolved in 70 parts by weight of Bis-GMA and 30 parts by weight of triethylene glycol dimethacrylate to prepare a polymerizable monomer A-1. The refractive index of the cured product of the polymerizable monomer A-1 was 1.554.

PREPARATION EXAMPLE 2

Preparation of Polymerizable Monomer A-2

A polymerizable monomer A-2 was prepared in the same manner as in Preparation Example 1 except that 75 parts by weight of Bis-GMA and 25 parts by weight of triethylene glycol dimethacrylate were used. The refractive index of the cured product of the polymerizable monomer A-2 was 1.559.

PREPARATION EXAMPLE 3

Preparation of Polymerizable Monomer A-3

A polymerizable monomer A-3 was prepared in the same manner as in Preparation Example 1 except that 25 parts by weight of Bis-GMA, 40 parts by weight of UDMA, and 35 parts by weight of triethylene glycol dimethacrylate were used. The refractive index of the cured product of the polymerizable monomer A-3 was 1.523.

PREPARATION EXAMPLE 4

Preparation of Polymerizable Monomer A-4

A polymerizable monomer A-4 was prepared in the same manner as in Preparation Example 1 except that 30 parts by weight of Bis-GMA, 40 parts by weight of UDMA, and 30 parts by weight of triethylene glycol dimethacrylate were used. The refractive index of the cured product of the polymerizable monomer A-4 was 1.530.

PREPARATION EXAMPLE 5

Preparation of Polymerizable Monomer A-5

A polymerizable monomer A-5 was prepared in the same manner as in Preparation Example 1 except that 65 parts by weight of Bis-GMA and 35 parts by weight of triethylene glycol dimethacrylate were used. The refractive index of the cured product of the polymerizable monomer A-5 was 1.549.

PREPARATION EXAMPLE 6

Preparation of Polymerizable Monomer A-6

A polymerizable monomer A-6 was prepared in the same manner as in Preparation Example 1 except that 70 parts by weight of UDMA and 30 parts by weight of triethylene glycol dimethacrylate were used. The refractive index of the cured product of the polymerizable monomer A-6 was 1.513.

PREPARATION EXAMPLE 7

Preparation of Amorphous Powder B-1

250 kg of zirconium oxychloride ($ZrOCl_2.8H_2O$, manufactured by Taiyo Koko Co., Ltd.) was added to 4375 kg of pure water at a temperature of 15° C. and they were stirred to dissolve zirconium oxychloride therein.

250 L of aqueous ammonia with a concentration of 15% by weight was added slowly, under stirring, to the aqueous solution of zirconium oxychloride to cause a neutralization reaction of the zirconium oxychloride under the temperature condition of 15° C. Thus, a slurry containing the precipitate of zirconium oxide hydrate was obtained. The pH of this slurry was 8.5.

Next, this slurry was filtered, and the resulting cake-like material was washed repeatedly with pure water to remove by-products of the neutralization reaction and unreacted substances. As a result, 860 kg of a cake-like material consisting of 10% by weight of zirconium oxide hydrate in terms of $ZrO_2$ and water was obtained.

Next, 45800 g of pure water was added to 5416 g of the cake-like material containing zirconium oxide hydrate, and further 1024 g of potassium hydroxide with a purity of 85% (manufactured by Kanto Chemical Co., Inc.) was added under stirring to the above mixture to make the mixture alkaline. Then, 10248 g of hydrogen peroxide solution containing 35% by weight of hydrogen peroxide (manufactured by Hayashi Pure Chemical Industries, Ltd.) was added to the mixture.

Furthermore, this mixed aqueous solution was allowed to stand, under stirring, for one hour to peptize the zirconium oxide hydrate in the aqueous solution. Then, 39991 g of ice water obtained by freezing pure water was added to the resulting aqueous solution to cool the temperature of the aqueous solution, which had been raised by the exothermic reaction, to 30° C. or lower. As a result, 102400 g of a mixed aqueous solution (hereinafter referred to as a "prepared solution 1A") with a pH of about 11 and containing 0.5% by weight of zirconium components in terms of $ZrO_2$ was obtained.

10 Kg of commercially available water glass (manufactured by AGC Si-Tec. Co., Ltd.) was diluted with 38 kg of pure water, and then was treated with a cation-exchange resin (manufactured by Mitsubishi Chemical Corporation) to remove alkali cations contained therein. Thus, 9 kg of a silicic acid solution with a pH of 3 and containing 4% by weight of $SiO_2$ was prepared. Then, 10768 g of the silicic acid solution and 14860 g of pure water were mixed with each other to prepare 25628 g of 2% by weight of a silicic acid solution.

Next, 47900 g of pure water was added to 3336 g of a silica sol containing 30% by weight of silica fine particles having an average particle size of 12 nm (SI-30, manufactured by Catalysts and Chemicals Industries Co., Ltd.), and the resulting mixture was stirred sufficiently. Thus, 51236 g of a silica sol containing 2% by weight of silica fine particles was obtained.

Next, the silica sol was heated to 90° C., and then 51200 g of the prepared solution 1A and 12814 g of the aqueous solution of the silicic acid solution were added slowly under stirring to the silica sol over 10 hours. As a result, 115250 g of a mixed aqueous solution with a pH of about 11 (hereinafter referred to as a prepared solution 1B-(1)) was obtained.

Next, the prepared solution 1B-(1) was treated with a cation-exchange resin (SK1BH, manufactured by Mitsubishi Chemical Corporation) to remove alkali cations contained therein. As a result, 117250 g of a mixed aqueous solution with a pH of about 9.5 (hereinafter referred to as a prepared solution 1C-(1)) was obtained.

Furthermore, 51200 g of the prepared solution 1A and 12814 g of the aqueous solution of the silicic acid solution were added slowly to the prepared solution 1C-(1) over 10 hours in the same manner as described above. As a result, 181264 g of a mixed aqueous solution with a pH of about 11 (hereinafter referred to as a prepared solution 1B-(2)) was obtained.

Next, the prepared solution 1B-(2) was treated with a cation-exchange resin (SK1BH, manufactured by Mitsubishi Chemical Corporation) to remove alkali cations contained therein. As a result, 182264 g of a mixed aqueous solution with a pH of about 9.5 (hereinafter referred to as a prepared solution 1C-(2)) was obtained.

Next, 100200 g of the prepared solution 1C-(2) was put in a stainless steel autoclave (manufactured by Taiatsu Techno Corporation), and was subjected to a hydrothermal treatment for 18 hours at a temperature of 165° C. As a result, 99750 g of a mixed aqueous solution (hereinafter referred to as a "prepared solution 1D) was obtained. This aqueous solution contained an amorphous powder in which the surfaces of silica-based fine particles were covered with coatings of an oxide containing a zirconium atom, a silicon atom, and an oxygen atom.

Next, the prepared solution 1D was pre-dried in a hot air dryer at 90° C. to obtain a pre-dried solid material 1B. This pre-dried solid material 1B was dried for another hour at 200° C., and then ground in a vibratory ball mill for 1.5 hours. Thus, a dried amorphous powder having a refractive index of 1.528 and an average particle size of 4.9 μm was obtained. 100 parts by weight of this dried amorphous powder was subjected to surface treatment with 30 parts by weight of γ-methacryloxypropyltrimethoxysilane (KBM 503, manufactured by Shin-Etsu Chemical Co., Ltd.). As a result, an amorphous powder B-1 was obtained.

PREPARATION EXAMPLE 8

Preparation of Amorphous Powder B-2

The pre-dried solid substance 1B obtained in Preparation Example 7 was placed in an electric furnace at 800° C. and subjected to heat treatment for 1 hour to obtain a calcined solid material 2B. This calcined solid material 2B was ground in a vibratory ball mill for 1.5 hours. Thus, a calcined amorphous powder having a refractive index of 1.549 and an average particle size of 6.3 μm was obtained. 100 parts by weight of the porous powder thus obtained was subjected to surface treatment with 25 parts by weight of γ-methacryloxypropyltrimethoxysilane. As a result, an amorphous powder B-2 was obtained.

PREPARATION EXAMPLE 9

Preparation of Amorphous Powder B-3

The calcined solid material 2B obtained in Preparation Example 8 was ground in a vibratory ball mill for 24 hours. Thus, a calcined amorphous powder having a refractive index of 1.549 and an average particle size of 1.9 μm was obtained. 100 parts by weight of the calcined amorphous powder thus obtained was subjected to surface treatment with 40 parts by weight of γ-methacryloxypropyltrimethoxysilane. As a result, an amorphous powder B-3 was obtained.

PREPARATION EXAMPLE 10

Preparation of Amorphous Powder B-4

The calcined solid material 2B obtained in Preparation Example 8 was ground in a vibratory ball mill for 1 hour. Thus, a calcined amorphous powder having a refractive index of 1.549 and an average particle size of 18.2 μm was obtained. 100 parts by weight of the calcined amorphous powder thus obtained was subjected to surface treatment with 20 parts by weight of γ-methacryloxypropyltrimethoxysilane. As a result, an amorphous powder B-4 was obtained.

PREPARATION EXAMPLE 11

Preparation of Amorphous Powder B-5

The calcined solid material 2B obtained in Preparation Example 8 was ground in a vibratory ball mill for 72 hours. Thus, a calcined amorphous powder having a refractive index of 1.549 and an average particle size of 0.7 μm was obtained. 100 parts by weight of the calcined amorphous powder thus obtained was subjected to surface treatment with 45 parts by weight of γ-methacryloxypropyltrimethoxysilane. As a result, an amorphous powder B-5 was obtained.

PREPARATION EXAMPLE 12

Preparation of Amorphous Powder B-6

The calcined solid material 2B obtained in Preparation Example 8 was ground in a vibratory ball mill for 30 minutes. Thus, a calcined amorphous powder having a refractive index of 1.549 and an average particle size of 25.4 μm was obtained. 100 parts by weight of the calcined amorphous powder thus obtained was subjected to surface treatment with 20 parts by weight of γ-methacryloxypropyltrimethoxysilane. As a result, an amorphous powder B-6 was obtained.

PREPARATION EXAMPLE 13

Preparation of Amorphous Powder B-7

The calcined solid material 2B obtained in Preparation Example 8 was ground in a vibratory ball mill for 1.5 hours. Thus, a calcined amorphous powder having a refractive index of 1.549 and an average particle size of 6.3 μm was obtained. 100 parts by weight of the porous powder thus obtained was subjected to surface treatment with 25 parts by weight of 11-methacryloyloxyundecyltrimethoxysilane. As a result, an amorphous powder B-7 was obtained.

PREPARATION EXAMPLE 14

Preparation of Aggregated Silica-Zirconia Powder

A pH-adjusted silica sol (with a pH of 2.5) prepared by adding dilute nitric acid to 147 g of a commercially available silica sol (Cataloid SI-30 having an average particle size of 10 to 14 nm, manufactured by Catalysts and Chemicals Industries Co. Ltd.), was added slowly dropwise to 85 g of zirconium acetate (zirconium acetate containing 15 to 16% Zr, manufactured by Sigma-Aldrich Corporation) to obtain a mixed sol. The sol thus obtained was put into a stainless steel tray, and then dried in a hot air dryer at 90° C. A solid material obtained by drying the sol was put into an alumina crucible and subjected to heat treatment in an electric furnace at 550° C. for 1 hour, and then the resulting solid material was ground in a vibratory ball mill for 90 minutes. Thus, an amorphous powder having a refractive index of 1.547 and an average particle size of 6.4 μm was obtained. 100 parts by weight of the amorphous powder thus obtained was subjected to surface treatment with 30 parts by weight of γ-methacryloxypropyltrimethoxysilane. As a result, an aggregated silica-zirconia powder was obtained.

PREPARATION EXAMPLE 15

Preparation of Inorganic Particles C-1

100 parts by weight of barium glass (8235UF 0.7, having an average particle size of 0.7 μm, manufactured by Schott) was subjected to surface treatment with 4 parts by weight of γ-methacryloxypropyltrimethoxysilane. As a result, inorganic particles C-1 were obtained. The refractive index of the inorganic particles C-1 was 1.550.

PREPARATION EXAMPLE 16

Preparation of Inorganic Particles C-2

Barium glass (8235UF 0.4, manufactured by Schott) was ground in a vibratory ball mill for 24 hours to obtain inorganic particles having an average particle size of 0.2 μm. 100 parts by weight of the inorganic particles thus obtained were subjected to surface treatment with 10 parts by weight of γ-methacryloxypropyltrimethoxysilane. As a result, inorganic particles C-2 were obtained. The refractive index of the inorganic particles C-2 was 1.550.

PREPARATION EXAMPLE 17

Preparation of Inorganic Particles C-3

100 parts by weight of barium glass (GM27884 NanoFine 180, having a particle size ranging from 0.05 to 0.5 μm and an average particle size of 0.18 μm, manufactured by Schott) was subjected to surface treatment with 10 parts by weight of γ-methacryloxypropyltrimethoxysilane. As a result, inorganic particles C-3 having an average particle size of 0.18 μm were obtained. The refractive index of the inorganic particles C-3 was 1.530.

PREPARATION EXAMPLE 18

Preparation of Inorganic Ultrafine Particles D-1

100 parts by weight of nearly spherical ultrafine particles having an average particle size of 20 nm (Aerosil 130, manufactured by Nippon Aerosil Corporation) were subjected to surface treatment with 40 parts by weight of γ-methacryloxypropyltrimethoxysilane. As a result, inorganic ultrafine particles D-1 were obtained.

PREPARATION EXAMPLE 19

Preparation of Inorganic Ultrafine Particles D-2

100 parts by weight of nearly spherical ultrafine particles having an average particle size of 40 nm (Aerosil OX 50, manufactured by Nippon Aerosil Corporation) were subjected to surface treatment with 7 parts by weight of γ-methacryloxypropyltrimethoxysilane. As a result, inorganic ultrafine particles D-2 were obtained.

PREPARATION EXAMPLE 20

Preparation of Inorganic Ultrafine Particles D-3

100 parts by weight of nearly spherical ultrafine particles having an average particle size of 20 nm (Aeroxide AluC, manufactured by Nippon Aerosil Corporation) were subjected to surface treatment with 20 parts by weight of γ-methacryloyloxypropyltrimethoxysilane. As a result, inorganic ultrafine particles D-3 were obtained.

PREPARATION EXAMPLE 21

Preparation of Inorganic Ultrafine Particles D-4

100 parts by weight of nearly spherical ultrafine particles having an average particle size of 7 nm (Aerosil 380, manufactured by Nippon Aerosil Corporation) were subjected to surface treatment with 50 parts by weight of γ-methacryloyloxypropyltrimethoxysilane. As a result, inorganic ultrafine particles D-4 were obtained.

EXAMPLES 1 TO 34 AND COMPARATIVE EXAMPLES 1 TO 5

The polymerizable monomer (A), the amorphous powder (B), the inorganic particles (C), and the inorganic ultrafine particles (D) were mixed and kneaded homogeneously in the amounts indicated in Tables 1 to 4 per 100 parts by weight of the polymerizable monomer (A) contained in each of the polymerizable monomers A-1 to A-6 prepared as above, and vacuum-degassed. As a result, the dental compositions of Examples 1 to 34 shown in Tables 1 to 3 and of Comparative Examples 1 to 5 shown in Table 4 were obtained. The properties of these dental compositions were evaluated in the manner described above. Tables 1 to 4 show the results.

TABLE 1

| | | | Examples | | | | | | |
|---|---|---|---|---|---|---|---|---|---|
| | | | 1 | 2 | 3 | 4 | 5 | 6 | 7 |
| Components of dental composition | Polymerizable monomer | A-1 | 100 | | | | 100 | | |
| | | A-2 | | 100 | | | | | 100 |
| | | A-3 | | | 100 | | | 100 | |
| | | A-4 | | | | 100 | | | |
| | Amorphous powder | B-1 | | | | | 400 | 400 | |
| | | B-2 | 400 | 400 | 400 | 400 | | | |
| | | B-3 | | | | | | | 400 |
| | | B-4 | | | | | | | |
| | Inorganic particles | C-1 | | | | | | | |
| | | C-2 | | | | | | | |
| | Inorganic ultrafine particles | D-1 | | | | | | | |
| | | D-2 | | | | | | | |
| Difference in refractive index between cured product of polymerizable monomer and amorphous powder | | | 0.005 | 0.01 | 0.026 | 0.019 | 0.026 | 0.005 | 0.01 |
| Degree of diffusion (D) | | | 0.012 | 0.110 | 0.420 | 0.284 | 0.418 | 0.011 | 0.112 |
| Degree of transparency (ΔL) | | | 47 | 40 | 31 | 37 | 31 | 48 | 40 |
| Handling properties | | | A | A | A | A | A | A | B |
| Flexural strength (MPa) | | | 134 | 136 | 133 | 134 | 130 | 131 | 132 |
| Polishability (%) | | | 84 | 85 | 83 | 84 | 82 | 81 | 83 |

| | | | Examples | | | | | |
|---|---|---|---|---|---|---|---|---|
| | | | 8 | 9 | 10 | 11 | 12 | 13 |
| Components of dental composition | Polymerizable monomer | A-1 | | | | | | |
| | | A-2 | 100 | 100 | 100 | 100 | 100 | 100 |
| | | A-3 | | | | | | |
| | | A-4 | | | | | | |

TABLE 1-continued

|  |  |  |  |  |  |  |  |
|---|---|---|---|---|---|---|---|
| Amorphous | B-1 |  |  |  |  |  |  |
| powder | B-2 |  | 200 | 200 | 200 | 200 | 50 |
|  | B-3 |  |  |  |  |  |  |
|  | B-4 | 400 |  |  |  |  |  |
| Inorganic | C-1 |  | 200 |  | 200 | 200 | 350 |
| particles | C-2 |  |  | 200 |  |  |  |
| Inorganic | D-1 |  |  |  | 20 |  |  |
| ultrafine | D-2 |  |  |  |  | 40 |  |
| particles |  |  |  |  |  |  |  |
| Difference in refractive index between cured product of polymerizable monomer and amorphous powder |  | 0.01 | 0.01 | 0.01 | 0.01 | 0.01 | 0.01 |
| Degree of diffusion (D) |  | 0.108 | 0.061 | 0.067 | 0.095 | 0.101 | 0.014 |
| Degree of transparency (ΔL) |  | 41 | 45 | 44 | 37 | 36 | 49 |
| Handling properties |  | B | A | A | A | A | B |
| Flexural strength (MPa) |  | 138 | 141 | 140 | 143 | 140 | 146 |
| Polishability (%) |  | 80 | 80 | 81 | 80 | 80 | 79 |

TABLE 2

|  |  |  | Examples |  |  |  |  |  |  |
|---|---|---|---|---|---|---|---|---|---|
|  |  |  | 14 | 15 | 16 | 17 | 18 | 19 | 20 |
| Components of dental composition | Polymerizable monomer | A-1 |  | 100 |  |  |  |  |  |
|  |  | A-2 |  |  | 100 |  |  |  | 100 |
|  |  | A-3 |  |  |  | 100 |  |  |  |
|  |  | A-4 | 100 |  |  |  | 100 | 100 |  |
|  | Amorphous powder | B-1 |  |  |  |  |  |  |  |
|  |  | B-2 |  | 350 | 350 | 350 | 350 |  | 400 |
|  |  | B-3 |  |  |  |  |  |  |  |
|  |  | B-4 |  |  |  |  |  |  |  |
|  |  | B-7 | 400 |  |  |  |  | 350 |  |
|  | Inorganic particles | C-1 |  |  |  |  |  |  |  |
|  |  | C-2 |  |  |  |  |  |  |  |
|  | Inorganic ultrafine particles | D-1 |  | 25 | 25 | 25 | 25 | 25 | 10 |
|  |  | D-2 |  |  |  |  |  |  |  |
|  |  | D-3 |  |  |  |  |  |  |  |
|  |  | D-4 |  |  |  |  |  |  |  |
| Difference in refractive index between cured product of polymerizable monomer and amorphous powder |  |  | 0.019 | 0.005 | 0.01 | 0.026 | 0.019 | 0.019 | 0.01 |
| Degree of diffusion (D) |  |  | 0.291 | 0.013 | 0.121 | 0.425 | 0.301 | 0.289 | 0.014 |
| Degree of transparency (ΔL) |  |  | 34 | 46 | 40 | 31 | 36 | 36 | 47 |
| Handling properties |  |  | B | A | A | A | A | A | A |
| Flexural strength (MPa) |  |  | 133 | 131 | 132 | 134 | 130 | 135 | 134 |
| Polishability (%) |  |  | 82 | 83 | 82 | 84 | 82 | 82 | 83 |

|  |  |  | Examples |  |  |  |  |  |
|---|---|---|---|---|---|---|---|---|
|  |  |  | 21 | 22 | 23 | 24 | 25 | 26 |
| Components of dental composition | Polymerizable monomer | A-1 |  |  |  |  |  |  |
|  |  | A-2 | 100 |  |  |  | 100 | 100 |
|  |  | A-3 |  |  |  |  |  |  |
|  |  | A-4 |  | 100 | 100 | 100 |  |  |
|  | Amorphous powder | B-1 |  |  |  |  |  |  |
|  |  | B-2 | 300 | 350 | 350 | 350 | 350 | 100 |
|  |  | B-3 |  |  |  |  |  |  |
|  |  | B-4 |  |  |  |  |  |  |
|  |  | B-7 |  |  |  |  |  |  |
|  | Inorganic particles | C-1 |  |  |  |  | 50 |  |
|  |  | C-2 |  |  |  |  |  | 400 |
|  | Inorganic ultrafine particles | D-1 | 75 |  |  |  |  |  |
|  |  | D-2 |  | 50 |  |  |  |  |
|  |  | D-3 |  |  | 20 |  |  |  |
|  |  | D-4 |  |  |  | 20 |  |  |
| Difference in refractive index between cured product of polymerizable monomer and amorphous powder |  |  | 0.01 | 0.019 | 0.019 | 0.019 | 0.026 | 0.026 |
| Degree of diffusion (D) |  |  | 0.019 | 0.302 | 0.296 | 0.271 | 0.410 | 0.018 |

TABLE 2-continued

|  |  |  |  |  |  |  |
|---|---|---|---|---|---|---|
| Degree of transparency (ΔL) | 34 | 34 | 36 | 38 | 32 | 36 |
| Handling properties | B | A | A | A | B | B |
| Flexural strength (MPa) | 128 | 138 | 134 | 131 | 132 | 148 |
| Polishability (%) | 80 | 81 | 84 | 83 | 82 | 79 |

TABLE 3

|  |  |  | Examples | | | | | | | |
|---|---|---|---|---|---|---|---|---|---|---|
|  |  |  | 27 | 28 | 29 | 30 | 31 | 32 | 33 | 34 |
| Components of dental composition | Polymerizable monomer | A-1 |  |  |  |  |  |  |  |  |
|  |  | A-2 |  |  |  |  |  |  |  |  |
|  |  | A-3 |  |  | 100 | 100 |  |  |  |  |
|  |  | A-4 | 100 | 100 |  |  | 100 | 100 | 100 | 100 |
|  | Amorphous powder | B-1 |  |  |  |  |  |  |  |  |
|  |  | B-2 | 300 | 300 | 100 | 100 |  |  | 300 | 300 |
|  |  | B-3 |  |  |  |  | 350 |  |  |  |
|  |  | B-4 |  |  |  |  |  | 350 |  |  |
|  |  | B-7 |  |  |  |  |  |  |  |  |
|  | Inorganic particles | C-1 |  | 100 |  | 300 |  |  |  |  |
|  |  | C-2 | 100 |  | 300 |  |  |  |  |  |
|  |  | C-3 |  |  |  |  |  |  | 100 | 100 |
|  | Inorganic ultrafine particles | D-1 | 20 |  |  |  | 25 | 25 |  | 20 |
|  |  | D-2 |  |  | 20 |  |  |  |  |  |
|  |  | D-3 |  | 20 |  |  |  |  |  |  |
|  |  | D-4 |  |  |  | 20 |  |  |  |  |
| Difference in refractive index between cured product of polymerizable monomer and amorphous powder |  |  | 0.019 | 0.019 | 0.026 | 0.026 | 0.019 | 0.019 | 0.019 | 0.019 |
| Degree of diffusion (D) |  |  | 0.273 | 0.269 | 0.037 | 0.034 | 0.298 | 0.303 | 0.291 | 0.301 |
| Degree of transparency (ΔL) |  |  | 41 | 42 | 34 | 35 | 37 | 38 | 38 | 37 |
| Handling properties |  |  | B | B | B | B | A | A | A | A |
| Flexural strength (MPa) |  |  | 140 | 142 | 146 | 149 | 135 | 139 | 137 | 141 |
| Polishbility (%) |  |  | 83 | 82 | 81 | 79 | 82 | 81 | 84 | 83 |

TABLE 4

|  |  |  | Comparative Examples | | | | |
|---|---|---|---|---|---|---|---|
|  |  |  | 1 | 2 | 3 | 4 | 5 |
| Components of dental composition | Polymerizable monomer | A-2 |  |  | 100 | 100 | 100 |
|  |  | A-5 | 100 |  |  |  |  |
|  |  | A-6 |  | 100 |  |  |  |
|  | Amorphous powder | B-1 |  |  |  |  |  |
|  |  | B-2 | 400 | 400 |  |  |  |
|  |  | B-3 |  |  |  |  |  |
|  |  | B-4 |  |  |  |  |  |
|  |  | B-5 |  |  |  | 400 |  |
|  |  | B-6 |  |  |  |  | 400 |
|  | Aggregated silica-zirconia powder |  |  |  | 400 |  |  |
|  | Inorganic particles | C-1 |  |  |  |  |  |
|  |  | C-2 |  |  |  |  |  |
|  | Inorganic ultrafine particles | D-1 |  |  |  |  |  |
|  |  | D-2 |  |  |  |  |  |
| Difference in refractive index between cured product of polymerizable monomer and amorphous powder |  |  | 0 | 0.036 | 0.012* | 0.010 | 0.010 |
| Degree of diffusion (D) |  |  | 0.001 | 0.601 | 0.004 | 0.109 | 0.110 |
| Degree of transparency (ΔL) |  |  | 52 | 19 | 36 | 41 | 40 |
| Handling properties |  |  | A | A | B | C | C |
| Flexural strength (MPa) |  |  | 135 | 138 | 121 | 131 | 136 |
| Polishability (%) |  |  | 83 | 82 | 78 | 82 | 83 |

*This value indicates the difference in refractive index between the cured product of the polymerizable monomer and the aggregated silica-zirconia powder.

These results show the following. The dental compositions of Examples each include a polymerizable monomer and an amorphous powder including silica-based fine particles and coatings of an oxide that cover the surfaces of the silica-based fine particles, the oxide contains a zirconium atom, a silicon atom, and an oxygen atom, and the difference in refractive index between the cured product of the polymerizable monomer and the amorphous powder is 0.005 to 0.03. These dental compositions of Examples each have optical properties suitable for matching natural teeth, particularly both the light diffusion property and transparency, and have excellent mechanical strength and polishability as well as excellent handling properties, compared with the dental compositions of Comparative Examples.

More specifically, it is seen from the comparison among Examples 1, 2 and 3 that as the difference in refractive index increases, the degree of diffusion increases and the degree of transparency decreases slightly. It is seen from the comparison among Examples 2, 9, 10 and 13 that the inorganic particles tend to increase the mechanical strength and transparency of the cured product. On the other hand, Comparative Examples 1 and 2, in which the differences in refractive index are beyond the specified range, show the following. The dental composition having a smaller refractive index difference has high transparency but its light diffusion property is insufficient, and the dental composition having a larger refractive index difference has insufficient transparency. Furthermore, the dental composition of Comparative Example 3, in which an aggregated silica-zirconia powder having a structure different from the specified structure of the present invention is used as a filler and the difference in refractive index between the cured product of the polymerizable monomer and the filler is in the range of 0.005 to 0.03, shows that it cannot achieve a good balance between the light diffusion property and the transparency and also is inferior in handling properties and mechanical strength to the dental composition using the amorphous powder having the specified structure.

These results suggest that the dental composition of the present invention has optical properties suitable for matching natural teeth, particularly both the light diffusion property and transparency, and has excellent mechanical strength and polishability as well as excellent handling properties.

INDUSTRIAL APPLICABILITY

The dental composition of the present invention can be used suitably as a substitute for a part of a natural tooth or an entire natural tooth in the field of dental treatment.

The invention claimed is:

1. A dental composition comprising:
   a polymerizable monomer (A);
   an amorphous powder (B) having an average particle size of 1 to 20 μm and including silica-based fine particles and coatings of an oxide that cover the surfaces of the silica-based fine particles, the oxide containing a zirconium atom, a silicon atom, and an oxygen atom, and
   inorganic particles (C) having an average particle size of from 0.1 to 1.0 μm
   wherein a difference in refractive index between a cured product of the polymerizable monomer (A) and the amorphous powder (B) is 0.005 to 0.03, and wherein the dental composition comprises 50 to 400 parts by weight of the inorganic particles (C) per 100 parts by weight of the polymerizable monomer (A).

2. The dental composition according to claim 1, wherein the dental composition comprises 50 to 400 parts by weight of the amorphous powder (B) per 100 parts by weight of the polymerizable monomer (A).

3. The dental composition according to claim 1, wherein the inorganic particles (C) comprise silica as a main component.

4. A dental composition comprising:
   a polymerizable monomer (A);
   an amorphous powder (B) having an average particle size of 1 to 20 μm and including silica-based fine particles and coatings of an oxide that cover the surfaces of the silica-based fine particles, the oxide comprising a zirconium atom, a silicon atom, and an oxygen atom, and
   inorganic ultrafine particles (D) having an average particle size of from 5 to 50 nm,
   wherein a difference in refractive index between a cured product of the polymerizable monomer (A) and the amorphous powder (B) is from 0.005 to 0.03.

5. The dental composition according to claim 4, wherein the dental composition comprises 10 to 50 parts by weight of the inorganic ultrafine particles (D) per 100 parts by weight of the polymerizable monomer (A).

6. The dental composition according to claim 1, wherein the silica-based fine particles of the amorphous powder (B) have an average particle size of 2 to 300 nm.

7. The dental composition according to claim 1, wherein in the amorphous powder (B), the oxide coating covers a plurality of the silica-based fine particles.

8. The dental composition according to claim 7, wherein the amorphous powder (B) has a structure in which the oxide coating of the silica-based fine particle and the oxide coating of the neighboring silica-based fine particle extend and are connected to each other.

9. The dental composition according to claim 7, wherein the amorphous powder (B) has a porous particle structure in which the oxide coatings are connected to each other to form an aggregate of the silica-based fine particles covered with the oxide coatings.

10. The dental composition according to claim 1, wherein the amorphous powder (B) is a calcined product.

11. The dental composition according to claim 1, wherein the surface of the amorphous powder (B) is treated with at least one organic metal compound selected from the group consisting of an organic silicon compound, an organic titanium compound, an organic zirconium compound, and an organic aluminum compound.

12. The dental composition according to claim 1, further comprising a polymerization initiator (E).

13. A composite resin using the dental composition according to claim 1.

14. The dental composition according to claim 4, wherein the silica-based fine particles of the amorphous powder (B) have an average particle size of from 2 to 300 nm.

15. The dental composition according to claim 4, wherein in the amorphous powder (B), the oxide coating covers a plurality of the silica-based fine particles.

16. The dental composition according to claim 15, wherein the amorphous powder (B) has a structure in which the oxide coating of the silica-based fine particle and the oxide coating of the neighboring silica-based fine particle extend and are connected to each other.

17. The dental composition according to claim 15, wherein the amorphous powder (B) has a porous particle structure in which the oxide coatings are connected to each other to form an aggregate of the silica-based fine particles covered with the oxide coatings.

18. The dental composition according to claim 4, wherein the amorphous powder (B) is a calcined product.

19. The dental composition according to claim 4, wherein the surface of the amorphous powder (B) is treated with at least one organic metal compound selected from the group consisting of an organic silicon compound, an organic titanium compound, an organic zirconium compound, and an organic aluminum compound.

20. A composite resin comprising the dental composition according to claim 4.

* * * * *